(12) United States Patent
Wang et al.

(10) Patent No.: US 12,306,098 B2
(45) Date of Patent: May 20, 2025

(54) METHODS AND RELATED ASPECTS FOR ANALYZING EXOSOMES

(71) Applicant: ARIZONA BOARD OF REGENTS ON BEHALF OF ARIZONA STATE UNIVERSITY, Scottsdale, AZ (US)

(72) Inventors: Shaopeng Wang, Chandler, AZ (US); Pengfei Zhang, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 197 days.

(21) Appl. No.: 18/204,735

(22) Filed: Jun. 1, 2023

(65) Prior Publication Data

US 2023/0408409 A1 Dec. 21, 2023

Related U.S. Application Data

(60) Provisional application No. 63/352,929, filed on Jun. 16, 2022.

(51) Int. Cl.
*G01N 21/55* (2014.01)
*G01N 33/543* (2006.01)
*G16B 15/00* (2019.01)

(52) U.S. Cl.
CPC ....... *G01N 21/55* (2013.01); *G01N 33/54373* (2013.01); *G16B 15/00* (2019.02); *G01N 2021/556* (2013.01)

(58) Field of Classification Search
CPC ............. G01N 21/55; G01N 33/54373; G01N 2021/556; G01N 21/51; G01N 21/553; G16B 15/00
See application file for complete search history.

(56) References Cited

U.S. PATENT DOCUMENTS

2024/0027325 A1* 1/2024 Chiu .................. G01N 15/1434

\* cited by examiner

*Primary Examiner* — Tony Ko
(74) *Attorney, Agent, or Firm* — MH2 Technology Law Group LLP

(57) ABSTRACT

Provided herein are methods of detecting exosomes, including unlabeled exosomes. In some embodiments, the methods include disposing a fluidic sample that comprises a plurality of exosomes in a chamber that is positioned at least partially within a fluidic device in which an inner surface of the chamber comprises a first set of exosome binding moieties that are capable of binding the exosomes. In some embodiments, the methods also include binding a portion of the plurality of exosomes to a portion of the first set of exosome binding moieties to produce surface-bound exosomes, introducing an incident light toward the inner surface of the chamber prior to, concurrent with, and/or after, producing the surface-bound exosomes, and detecting light scattered by the surface-bound exosomes to produce a set of exosome imaging data. Related fluidic devices, systems, and computer readable media are also provided.

20 Claims, 16 Drawing Sheets

METHODS AND RELATED ASPECTS FOR ANALYZING EXOSOMES

CROSS-REFERENCE TO RELATED APPLICATIONS

This application claims the benefit of U.S. Provisional Patent Application Ser. No. 63/352,929, filed Jun. 16, 2022, the disclosure of which is incorporated herein by reference.

STATEMENT OF GOVERNMENT SUPPORT

This invention was made with government support under R33 CA235294 and RO1 GM107165 awarded by the National Institutes of Health. The government has certain rights in the invention.

BACKGROUND

All prokaryotic and eukaryotic cells shed massive quantities of extracellular vesicles (EVs) into the circulation. Exosome is one particular type of EV with a diameter range of 30 to 150 nm (average ~100 nm) and serves as an intercellular transit system to regulate distant cell physiology and activity. Due to the endosomal origin mechanism, the constituents of exosomes can reflect the type of cells where they are released. Thus, rapid exosome analysis provides an effortless and promising way to evaluate the health conditions without biopsying the tissues.

Traditional exosome biomarker analysis relies on the western blot technique, which requires enormous amounts of sample and extensive post-labelling processes for detection, making it impractical for rapid detection. Several approaches have been developed in the recent decade for rapid exosome biomarker analysis, such as miniaturized nuclear magnetic resonance, nanoplasmonic array sensor, nanoplasmonic enhanced scattering, target magnification with reagent-loaded liposomes, and surface plasmon resonance (SPR) microscopy. Among these technologies, SPR microscopy allows the analysis of both exosome biomarkers and size distribution, while an additional nanoparticle tracking analysis (NTA) measurement was required to achieve exosome size information for other approaches. Thus, it provides an economical and efficient choice for multiplexed rapid exosome analysis in clinical applications. However, there are still some limitations to the wider application of SPR microscopy. First, the SPR microscopy has a parabolic tail-shaped point spread function, resulting in low spatial resolution, and making it challenging to process the images automatically with regular image processing tool. Second, the SPR microscopy is constructed on a total internal reflection fluorescence objective, which is expensive and can only provide a semi-circular field of view of up to 300 µm in diameter, resulting in a limited throughput. Third, the SPR microscopy currently only allows the analysis of the exosome binding to the antibody immobilized on the sensor surface, and it is hard to configure different antibodies on a small field of view. Therefore, multiplexed protein marker analysis is hard to be achieved on current SPR microscopy.

Accordingly, there is a need for additional techniques for detecting and analyzing exosomes.

SUMMARY

This disclosure describes fluidic devices, systems, computer readable media, and methods for detecting and analyzing exosomes (e.g., unlabeled exosomes). In some embodiments, for example, the methods and related aspects of the present disclosure implement a plasmonic scattering microscopy (PSM) technology for imaging exosomes, analysing multiple protein biomarkers, and quantifying their binding kinetics without labels. PSM was first developed to realize label-free single-molecule imaging on SPR microscopy, where it has been demonstrated that PSM can provide Gaussian distributed point spread function for high spatial resolution and automatic image processing with conventional software such as ImageJ. Some aspects of the present disclosure show that the PSM constructed on a popular prism coupled SPR system can provide up to ~40 and 100 times larger field of view than the SPR microscopy and NTA instrument respectively, thus providing high throughput for analysing the highly heterogeneous sizes of exosomes. Furthermore, the large-view PSM can also provide sufficient sensitivity to monitor the process of antibody binding to exosomes absorbed on the sensor surface, thus allowing the multiplexed protein marker analysis by simply flowing the antibody in a serial. These and other attributes of the present disclosure will be apparent upon a complete review of the specification, including the accompanying figures.

In one aspect, the present disclosure provides a method of detecting an exosome (e.g., an unlabeled exosome). The method includes disposing a fluidic sample that comprises a plurality of exosomes in a chamber that is positioned at least partially within a fluidic device, wherein at least one inner surface of the chamber comprises at least a first set of exosome binding moieties that are capable of binding the exosomes. The method also includes binding at least a portion of the plurality of exosomes to at least a portion of the first set of exosome binding moieties to produce one or more surface-bound exosomes, introducing an incident light toward the inner surface of the chamber concurrent with, and/or after, producing the surface-bound exosomes, and detecting light scattered by the surface-bound exosomes to produce a set of exosome imaging data.

In some embodiments, the disposing step comprises flowing the fluidic sample at least partially through the chamber. In some embodiments, the plurality of exosomes is unlabeled. In some embodiments, the first set of exosome binding moieties are selected from the group consisting of: a first set of antibodies, a first set of aptamers, and a first set of receptors. In some embodiments, the method comprises detecting the light scattered by the surface-bound exosomes over a duration to produce the set of exosome imaging data.

In some embodiments, the method further comprises counting a number of individual surface-bound exosomes over the duration to produce a count and fitting the count with a binding model to determine kinetic constants and/or at least one affinity value. In some embodiments, the duration comprises about 15 minutes, about 10 minutes, about 5 minutes, or less time. In some embodiments, the method comprises detecting the light scattered by the surface-bound exosomes using at least one plasmonic scattering microscopy (PSM) technique.

In some embodiments, the plurality of exosomes comprises one or more biomarkers and wherein the method comprises quantifying the biomarkers and/or binding kinetics thereof using the set of exosome imaging data. In some embodiments, the biomarkers are selected from the group consisting of: a protein, a nucleic acid, a carbohydrate, a lipid, and a combination thereof. In some embodiments, the method comprises differentiating at least some of the plurality of exosomes from other extracellular vesicles in the fluidic sample using the set of exosome imaging data. In some embodiments, the method comprises determining a cellular origin of one or more of the surface-bound exosomes using the set of exosome imaging data. In some embodiments, the cellular origin comprises a diseased cell or a non-diseased cell. In some embodiments, the diseased cell comprises a cancer cell.

In some embodiments, the method comprises determining one or more properties of surface-bound exosomes selected from the group consisting of: an exosome size distribution, an exosome biomarker identity, and an exosome biomarker binding property. In some embodiments, the set of exosome imaging data comprises image intensity variation. In some embodiments, the method comprises obtaining the fluidic sample from a subject prior to the disposing step (e.g., a blood sample, a urine sample, a cerebrospinal fluid sample, a sputum sample, or the like).

In some embodiments, the method further comprises disposing at least a second set of exosome binding moieties that are capable of binding the exosomes in the chamber prior to, concurrent with, or after producing the surface-bound exosomes, wherein at least a portion of the second set of exosome binding moieties bind to at least some of the plurality of exosomes. In some embodiments, the disposing step comprises flowing the second set of exosome binding moieties at least partially through the chamber. In some embodiments, the method comprises flowing different sets of exosome binding moieties in series at least partially through the chamber. In some embodiments, the second set of exosome binding moieties are selected from the group consisting of: a second set of antibodies, a second set of aptamers, and a second set of receptors. In some embodiments, the first and second sets of exosome binding moieties are different from one another.

In some embodiments, the inner surface of the chamber is coated with a metallic layer. In some embodiments, the metallic layer comprises gold (Au). In some embodiments, an incident angle of the incident light is selected to create surface plasmon resonance on the metallic layer. In some embodiments, a roughness of the inner surface is selected such that light scattered by the inner surface interferes with at least some of the light scattered by the surface-bound exosomes. In some embodiments, the method comprises producing the surface-bound exosomes and detecting the light scattered by the surface-bound exosomes substantially simultaneously. In some embodiments, the method comprises detecting the light scattered by the surface-bound exosomes in substantially real-time. In some embodiments, the detecting step comprises detecting evanescent light scattered by individual surface-bound exosomes. In some embodiments, the method comprises introducing the incident light toward the inner surface via an outer surface of the fluidic device. In some embodiments, the set of exosome imaging data comprises video data. In some embodiments, the fluidic device comprises at least one inlet port and at least one outlet port that both fluidly communicate with the chamber and wherein the method further comprises flowing the fluidic sample into the chamber via the inlet port and out of the chamber via outlet port.

In another aspect, the present disclosure provides a fluidic device that includes a body structure that defines at least one chamber disposed substantially within the body structure, wherein the chamber comprises a fluidic sample that comprises a plurality of exosomes and an inner surface that is coated with a metallic layer that is configured to create surface plasmon resonance when incident light is introduced toward the inner surface at a suitable incident angle via an outer surface of the chamber, and wherein the metallic layer comprises at least a first set of exosome binding moieties. In some embodiments, the fluidic device further comprises at least one inlet port and at least one outlet port that both fluidly communicate with the chamber. In some embodiments, the metallic layer comprises gold (Au). In some embodiments, the first set of exosome binding moieties is selected from the group consisting of: antibodies, aptamers, and receptors.

In another aspect, the present disclosure provides a system for detecting exosomes. The system includes a fluidic device receiving area configured to receive a fluidic device that comprises a body structure that defines at least one chamber disposed substantially within the body structure, wherein the chamber comprises an inner surface that is coated with a metallic layer that is configured to create surface plasmon resonance when incident light is introduced toward the inner surface at a suitable incident angle via an outer surface of the chamber, and wherein the metallic layer comprises at least a first set of exosome binding moieties. The system also includes a light source configured to introduce an incident light toward the fluidic device receiving area, and a detector configured to collect light scattered by surface-bound exosomes when the fluidic device is received in the fluidic device receiving area and the incident light is introduced from the light source. The system also includes a controller that comprises, or is capable of accessing, computer readable media comprising non-transitory computer-executable instructions which, when executed by at least one electronic processor, perform at least: disposing a fluidic sample that comprises a plurality of exosomes in the chamber of the fluidic device such that at least a portion of the plurality of exosomes bind to at least a portion of the first set of exosome binding moieties to produce one or more surface-bound exosomes when the fluidic device is received in the fluidic device receiving area; introducing the incident light from the light source at the suitable incident angle toward the inner surface of the chamber when the fluidic device is received in the fluidic device receiving area; and detecting light scattered by the surface-bound exosomes over a duration to produce a set of exosome imaging data to thereby detect the exosomes using the detector when the fluidic device is received in the fluidic device receiving area.

In another aspect, the present disclosure provides a computer readable media comprising non-transitory computer executable instructions which, when executed by at least one electronic processor, perform at least: disposing a fluidic sample that comprises a plurality of exosomes in a chamber of a fluidic device, wherein the chamber comprises an inner surface that is coated with a metallic layer that is configured to create surface plasmon resonance when incident light is introduced toward the inner surface at a suitable incident angle via an outer surface of the chamber, and wherein the metallic layer comprises at least a first set of exosome binding moieties such that at least a portion of the plurality of exosomes bind to at least a portion of the first set of exosome binding moieties to produce one or more surface-bound exosomes; introducing an incident light from a light source toward the inner surface of the chamber; and detecting light scattered by the surface-bound exosomes over a duration to produce a set of exosome imaging data to thereby detect the exosomes biomolecules using a detector.

In some embodiments of the systems and computer readable media disclosed herein, the set of exosome imaging data comprises video data. In some embodiments of the systems and computer readable media disclosed herein, the duration comprises about 15 minutes, about 10 minutes, about 5 minutes, or less time.

In some embodiments of the systems and computer readable media disclosed herein, the non-transitory computer-executable instructions which, when executed by the electronic processor, further perform at least: counting a number of individual surface-bound exosomes over the duration to produce a count and fitting the count with a binding model to determine kinetic constants and/or at least one affinity value. In some embodiments of the systems and computer readable media disclosed herein, the non-transitory computer-executable instructions which, when executed by the electronic processor, further perform at least: quantifying biomarkers of the exosomes and/or binding kinetics thereof using the set of exosome imaging data.

In some embodiments of the systems and computer readable media disclosed herein, the non-transitory computer-executable instructions which, when executed by the electronic processor, further perform at least: differentiating at least some of the plurality of exosomes from other extracellular vesicles in the fluidic sample using the set of exosome imaging data. In some embodiments of the systems and computer readable media disclosed herein, the non-transitory computer-executable instructions which, when executed by the electronic processor, further perform at least: determining a cellular origin of one or more of the surface-bound exosomes using the set of exosome imaging data. In some embodiments of the systems and computer readable media disclosed herein, the fluidic device comprises at least one inlet port and at least one outlet port that both fluidly communicate with the chamber and wherein the non-transitory computer-executable instructions which, when executed by the electronic processor, further perform at least: flowing the fluidic sample into the chamber via the inlet port and out of the chamber via outlet port using at least one fluid conveyance device.

In some embodiments of the systems and computer readable media disclosed herein, the non-transitory computer-executable instructions which, when executed by the electronic processor, further perform at least: determining one or more properties of surface-bound exosomes selected from the group consisting of: an exosome size distribution, an exosome biomarker identity, and an exosome biomarker binding property. In some embodiments of the systems and computer readable media disclosed herein, the non-transitory computer-executable instructions which, when executed by the electronic processor, further perform at least: disposing at least a second set of exosome binding moieties that are capable of binding the exosomes in the chamber prior to, concurrent with, or after producing the surface-bound exosomes, wherein at least a portion of the second set of exosome binding moieties bind to at least some of the plurality of exosomes. In some embodiments of the systems and computer readable media disclosed herein, the non-transitory computer-executable instructions which, when executed by the electronic processor, further perform at least: flowing different sets of exosome binding moieties in series at least partially through the chamber.

DEFINITIONS

Figure 1A:
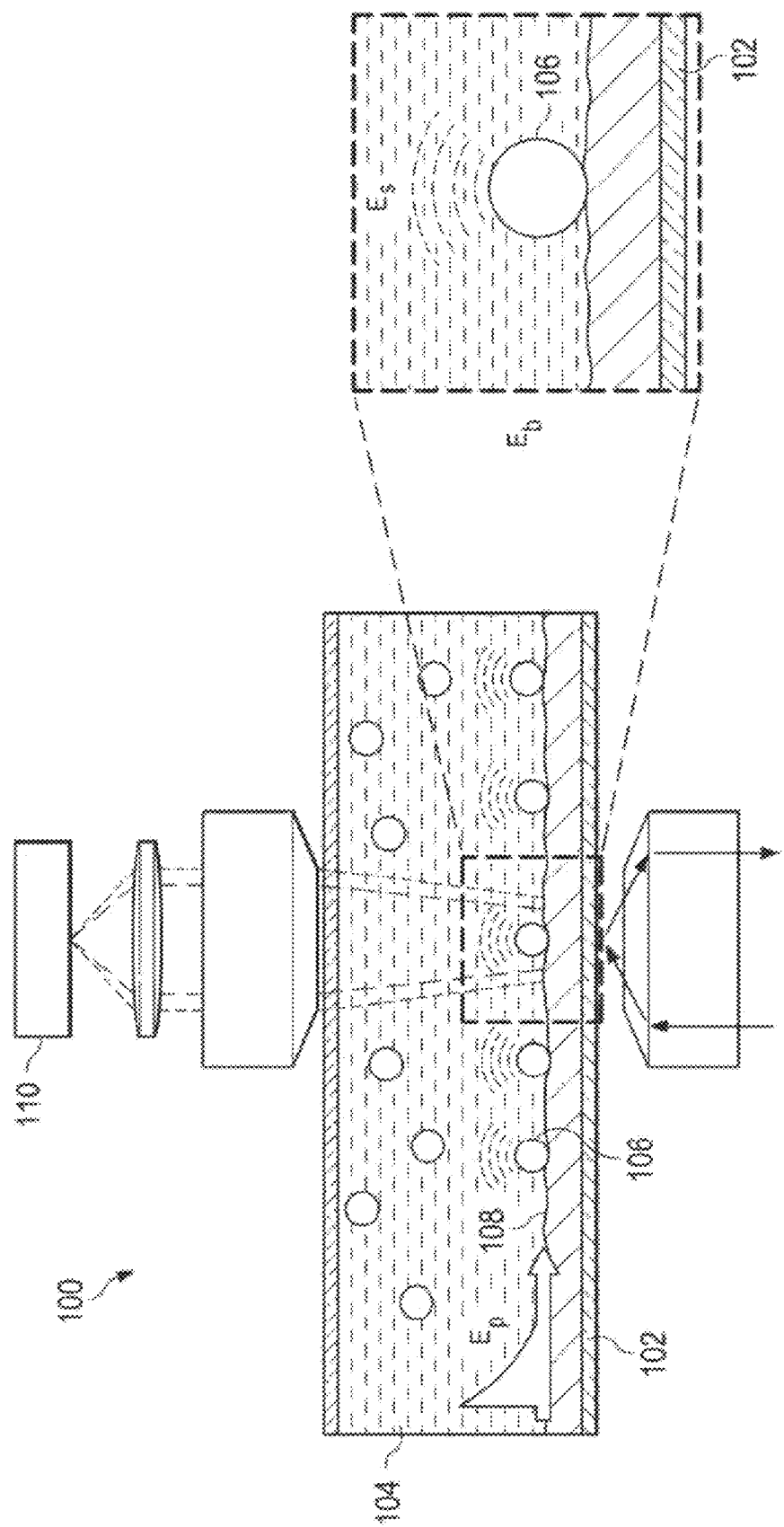
FIGS. 1A and 1B schematically show an exemplary objective-based plasmonic imaging system that can be used to detect single exosome binding to the surface of a sensor according to some aspects disclosed herein.

In order for the present disclosure to be more readily understood, certain terms are first defined below. Additional definitions for the following terms and other terms may be set forth throughout the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, fluidic devices, systems, and computer readable media, the following terminology, and grammatical variants thereof, will be used in accordance with the definitions set forth below.

About: As used herein, "about" or "approximately" as applied to one or more values or elements of interest, refers to a value or element that is similar to a stated reference value or element. In certain embodiments, the term "about" or "approximately" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Antibody: As used herein, the term "antibody" refers to an immunoglobulin or an antigen-binding domain thereof. The term includes but is not limited to polyclonal, monoclonal, monospecific, polyspecific, non-specific, humanized, human, canonized, canine, felinized, feline, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda. The term "monoclonal antibody" refers to an antibody that displays a single binding specificity and affinity for a particular target, e.g., epitope.

Binding: As used herein, the term "binding", typically refers to a non-covalent association between or among two or more entities.

Detect: As used herein, "detect," "detecting," or "detection" refers to an act of determining the existence or presence of one or more analytes in a given sample.

Exosome: As used herein, "exosome" refers to a nanometer-size extracellular vesicle that transports proteins, RNAs, and/or lipids from a cellular origin.

Exosome Binding Moiety: As used herein, "exosome binding moiety" refers to a molecule or compound that is capable of binding to an exosome, for example, via a protein or other biomolecule displayed on a surface of the exosome. Exemplary exosome binding moieties include antibodies, aptamers, receptors, and/or the like.

In some embodiments: As used herein, the term "in some embodiments" refers to embodiments of all aspects of the disclosure, unless the context clearly indicates otherwise.

Moiety: As used herein, "moiety" in the context of chemical compounds or structures refers to one of the portions into which the compound or structure is or can be divided (e.g., a functional group, a substituent group, or the like).

Nucleic Acid: As used herein, "nucleic acid" refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids can also include nucleotide analogs (e.g., bromodeoxyuridine (BrdU)), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA, cfDNA, ctDNA, or any combination thereof.

Protein: As used herein, "protein" or "polypeptide" refers to a polymer of at least two amino acids attached to one another by a peptide bond. Examples of proteins include enzymes, hormones, antibodies, and fragments thereof.

Sample: As used herein, "sample" or "fluidic sample" refers to a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide), which is assayed as described herein. A sample may also be any body fluid or excretion (for example, but not limited to, blood, urine, stool, saliva, tears, bile) that contains cells, cell components, or non-cellular fractions.

Subject: As used herein, the term "subject" means any member of the animal kingdom. In some embodiments, "subject" refers to humans. In some embodiments, "subject" refers to non-human animals. In some embodiments, subjects include, but are not limited to, mammals, birds, reptiles, amphibians, fish, insects, and/or worms. In some embodiments, the non-human subject is a mammal (e.g., a rodent, a mouse, a rat, a rabbit, a ferret, a monkey, a dog, a cat, a sheep, cattle, a primate, and/or a pig). In some embodiments, a subject may be a transgenic animal, genetically-engineered animal, and/or a clone. In some embodiments, the subject is an adult, an adolescent or an infant. In some embodiments, terms "individual" or "patient" are used and are intended to be interchangeable with "subject."

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

System: As used herein, "system" in the context of analytical instrumentation refers a group of objects and/or devices that form a network for performing a desired objective.

DETAILED DESCRIPTION

Exosome analysis is a promising tool for clinical and biological research applications. However, detection and biomarker quantification of exosomes is technically challenging because they are small and highly heterogeneous. In some aspect, the present disclosure provides an optical approach for imaging exosomes and quantifying their protein markers without labels using plasmonic scattering microscopy (PSM). PSM can select exosomes from extracellular vesicles with exosome binding moiety modified (e.g., antibody modified) sensor surfaces and provide a millimeter-scale field of view, which is ~40 and 100 times larger than the surface plasmon resonance (SPR) microscopy and nanoparticle tracking analysis instrument respectively, thus providing high throughput for exosome size distribution analysis. Furthermore, PSM can provide high sensitivity for monitoring the response of exosomes to the antibodies, thus allowing for analyzing content levels and binding kinetics of multiple biomarkers by, for example, serially flowing different antibody solutions onto the exosomes. As a further example, PSM can be easily constructed on a popular prism-coupled SPR system with commercially available components. These and other attributes of the present disclosure will be apparent upon a complete review of the specification, including the accompanying figures.

In some embodiments, the systems and methods described herein include implementations of near field optical imaging in which the near field is created by surface plasmon resonance (SPR) or total internal reflection (TIF).

Rather than detection of reflected light, however, scattered light from the sample molecules and sensor surface is detected. Light scattered by a molecule in free space scales with the $6^{th}$ power of the molecular diameter. For this reason, the scattered light intensity diminishes quickly with the molecular size, making it difficult to image single molecules. To overcome this issue, a sensor surface with a selected roughness is used, such that the sensor surface scatters light with a magnitude comparable with that of the scattered light from the target single molecules. There are different ways to define surface roughness, and one of which is given by $$\sqrt{\frac{1}{n}\sum_{i=1}^{n} y_i^2} \quad (1)$$

where $y_i$ is the height at position i, and n is the number of positions. Using this definition, the surface roughness of a gold surface is ~1.5 nm.

In some implementations, a roughness of the sensor surface is in a range of about 1 nm to about 100 nm. The interference of light scattered from the protein and sensor surface produces an image contrast that scales with the $3^{rd}$ power of the molecular diameter. This slows down the decay in image contrast with the molecular size, which favors imaging of small objects (e.g., single exosomes, single protein molecules, etc.).

Rough features and impurities on the sensor surface, and features associated with imperfect optics, all contribute to image contrast, which can mask weak images of single exosomes or molecules. As described herein, a differential-integral imaging processing algorithm is used to subtract out background features that contribute to image contrast above from each frame of the time sequence images and integrate the differential images to recover the binding and unbinding of single exosomes on the sensor surface. A drift or motion correction algorithm is introduced to track the drift or motion pattern of one or more features on the sensor surface and correct the drift or motion from each image frame, thereby reducing the impact of drift in position of the sensor surface or the optics or mechanical vibrations of the environment. Binding kinetics are assessed by counting the individual exosomes on the sensor surface. This digital counting approach allows a precise measurement of binding kinetics. In addition, this approach obviates the need to measure the shift in the surface plasmon resonance angle (determined not only the number of the exosomes that bind to the sensor surface, but also by the size of the exosomes) either directly or indirectly.

SPR-based single exosome analysis. Implementations include plasmonic imaging systems and methods for SPR-based single exosome analysis. In some cases, the plasmonic imaging system includes an objective. In some cases, the plasmonic imaging system includes an optical prism rather than an objective.

FIG. 1A is a schematic of objective-based plasmonic imaging system 100 that can be used to detect single exosome binding to the surface of a sensor. Surface plasmonic waves ($E_p$) are excited by light from the bottom of a gold-coated glass slide and scattering of the plasmonic waves by a particle or exosome ($E_s$) and by the gold surface ($E_b$) is collected from the top to form a plasmonic scattering microscopy (PSM) image. In one example, a sensor includes a metal (e.g., gold) coated glass substrate 102. A solution 104 of the target exosome 106 is introduced to the sensing surface (e.g., via a flow cell). The sensor surface can be functionalized with exosome binding moieties 108 for detection of target exosomes. The light scattered from the exosomes is collected from the top camera 110. The conventional surface plasmon resonance image can be obtained from a bottom camera simultaneously.

In some implementations, the objective of the system in FIG. 1A is replaced with an optical prism. The prism has a top surface on which the sensor is placed. The prism also has a flat surface for the introduction of incident light and a second flat surface for light reflected from the sensor surface to exit the prism.

Figure 1B:
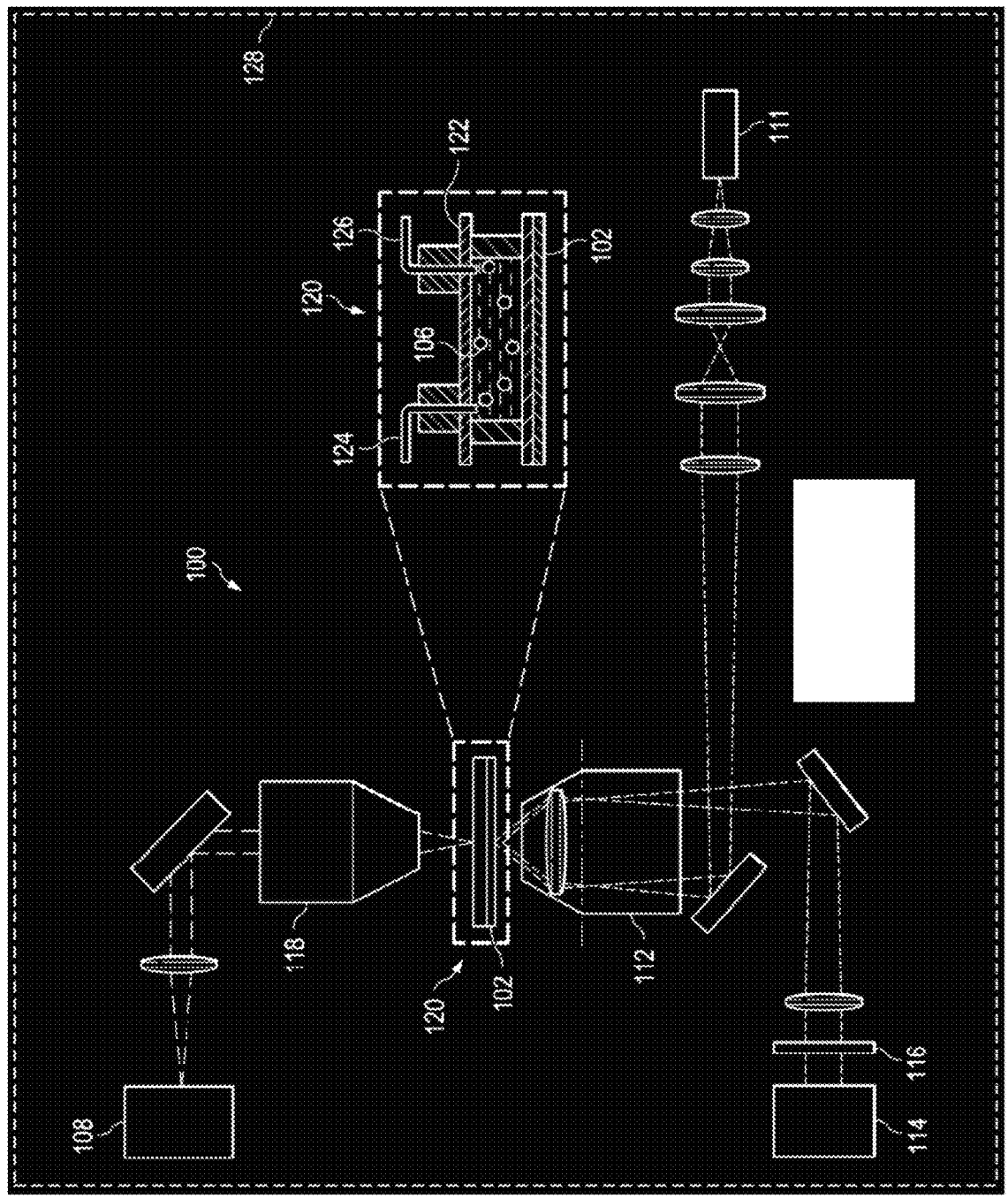

FIG. 1B is a more detailed view of objective-based plasmonic imaging system 100. Optical setup for simultaneous PSM and SPR imaging, where light from a superluminescent diode (SLD) 111 is conditioned and directed via a 60× objective (NA=1.49) 112 onto a gold-coated glass slide 102 mounted on the objective via refractive index matching oil. Light reflected from the gold-coated glass slide 102 is detected by camera 114 (Pike F-032B), which is equipped with an optical attenuator 116 (ND30A, Thorlabs, Newton, NJ) to avoid overexposure. The incident light angle is adjusted to surface plasmon resonance, at which the reflected light reaches a minimum. Simultaneously, light scattered from the gold surface is collected by a 50× objective (NA=0.42) 118 and detected by camera 108 (MQ003MG-CM, XIMEA) placed on top of the gold surface. The incident light intensity is 3 kW/cm$^2$ or less. Camera 114 measures the traditional SPR and camera 108 records PSM images. Flow cell 120 includes gold-coated glass slide 102, cover glass 122, inlet 124, and outlet 126. In one embodiment, a distance between gold-coated glass slide 102 and cover glass 122 is about 50 microns. However, this distance can be different in other embodiments.

System 100 can include controller 128. Controller 128 can be configured to control one or more components of system 100 (e.g., cameras 108, 114, SLD 111), to control fluid flow to and away from system 100, and to process data or images collected one or more components of system 100 (e.g., cameras 108, 114). In some cases, controller 128 can be used to correct for mechanical drift in system 100.

In one example, gold-coated glass slides were prepared by evaporating 2 nm thick chromium on BK-7 glass slides, followed by 47 nm gold. Before loading into the vacuum chamber for chromium and gold evaporation, the BK-7 glass slides were cleaned by acetone and by deionized water thoroughly. The gold surfaces were examined by Atomic Force Microscopy (AFM), showing islands of variable sizes.

TIF-based single exosome analysis. Systems for TIF-based exosome analysis can be similar to those for SPR-based single exosome analysis, with a sensor surface that is free of a metallic coating. When the incident angle is near or larger than a critical angle, it is totally reflected from the sensor surface, which has been referred to as total internal reflection (TIF). Under this condition, an evanescent field (also referred to as near field) appears on the sensor surface, which decays exponentially into the solution on top of the sensor surface. As in the SPR implementations, this evanescent field is scattered by single exosomes on the sensor surface, and the interference light scattered by the single exosomes and by the sensor surface produces image contrast.

Effect of heating due to incident light. To maximize the signal to noise ratio, high incident light intensity is preferred, which, however, causes heating of the sensor surface and leading to instability of the optical system and structure of the target exosomes. This problem can be overcome as described herein by using the same fluidics for flowing in and out sample molecules to cool down the heating.

Single exosomes are directly imaged with a SPR imaging system, and detected and identified based on their sizes and specific binding to the corresponding antibodies or other exosome binding moieties. Quantification of exosome binding kinetics is demonstrated by digitally counting and analyzing the binding and unbinding of individual exosomes.

The SPR imaging system has several unique features. First, the evanescent field intensity is localized within ~100 nm from the SPR sensor surface (e.g., gold-coated glass slide), making it immune to interference of molecules and impurities in the bulk solution, thus particularly suitable for studying surface binding. Second, there is a large enhancement (20-30 times) in the field near the sensor surface, which is responsible for the high sensitivity of SPR. Finally, the resonance condition of SPR depends on the refractive index near the sensor surface, such that surface charging, small molecules or ions, and biochemical reactions that do not scatter light strongly can also be measured with the same setup from the simultaneously recorded traditional SPR images.

Referring to FIG. 1A, surface plasmonic waves are excited by directing light at an appropriate angle via an oil-immersion objective onto a gold-coated glass slide placed on the objective. In traditional SPR, light reflected from the gold surface is collected to form an SPR image, which is described by $$I \sim |E_i + E_p + E_r|^2$$

where $E_p$ is the plasmonic wave excited by the incident light, $E_s$ describes the scattering of the plasmonic wave by an exosome on the sensor surface, and $E_r$ is the reflection of the incident wave from the backside of the gold surface. The SPR image contrast is determined by the interference between the planar plasmonic wave and the spherical scattered plasmonic wave, given by $2|E_p||E_s|\cos(\Theta)$, where Q is the phase difference between the two waves, which produces a spot at the location of the exosome with a parabolic tail. $E_s$ is proportional to the optical polarizability of the exosome, which scales with the mass of the exosome or $d^3$, where d is the diameter.

$E_r$ in Eq. 2 produces a large background in the SPR image, which masks the weak scattered wave ($E_s$) from a single exosome. To overcome this difficulty, plasmonic waves scattered by the exosome are imaged with a second objective placed on top of the sample, in addition to recording the traditional SPR images from the bottom. This avoids the collection of the strong reflection and also eliminates the parabolic tail, providing a high contrast image of the exosome. At first glance, the image contrast should scale according to $|E_s|^2 \sim d^6$. This would lead to a rapid drop in the image contrast with decreasing d, making it challenging to detect small exosomes. However, the gold surface is not atomically flat. Atomic Force Microscopy (AFM) has revealed nm-scaled gold islands, which scatter the surface plasmonic waves and produce a background ($E_b$) also collected by the top objective. Consequently, the plasmonic image is given by $$I \sim |E_b + E_o|^2 = |E_b|^2 + 2|E_b||E_s|\cos(\beta) + |E_s|^2, \quad (3)$$

where β is the phase difference between light scattered by the exosome and by the gold surface. The interference term, $2|E_b||E_s|\cos(\beta)$, in Eq.3 produces image contrast that scales with $d^3$, or the mass of the exosome. To differentiate this plasmonic imaging method from the traditional SPR imaging, it is referred to as PSM.

To obtain a high contrast PSM image, $|E_b|^2$ is removed from Eq. 3, which is achieved with the following imaging processing flow. Starting from the raw images captured with a high frame rate, the image frames are averaged (e.g., over 50 ms) to remove pixel and other random noise in the images. Differential images are then obtained by subtracting a previous frame from each frame, or I(N)−I(N−1), where I(N) and I(N−1) are the $N^{th}$ and $(N-1)^{th}$ image frames. The subtraction removes background features and captures the binding of an exosome to the surface on $N^{th}$ image frame. To view all the exosomes on the surface on $N^{th}$ frame, the differential images are integrated from 1 to N. Due to thermal and mechanical drift of the optical system, a drift correction mechanism is introduced to ensure effective removal of the background.

Figure 2:
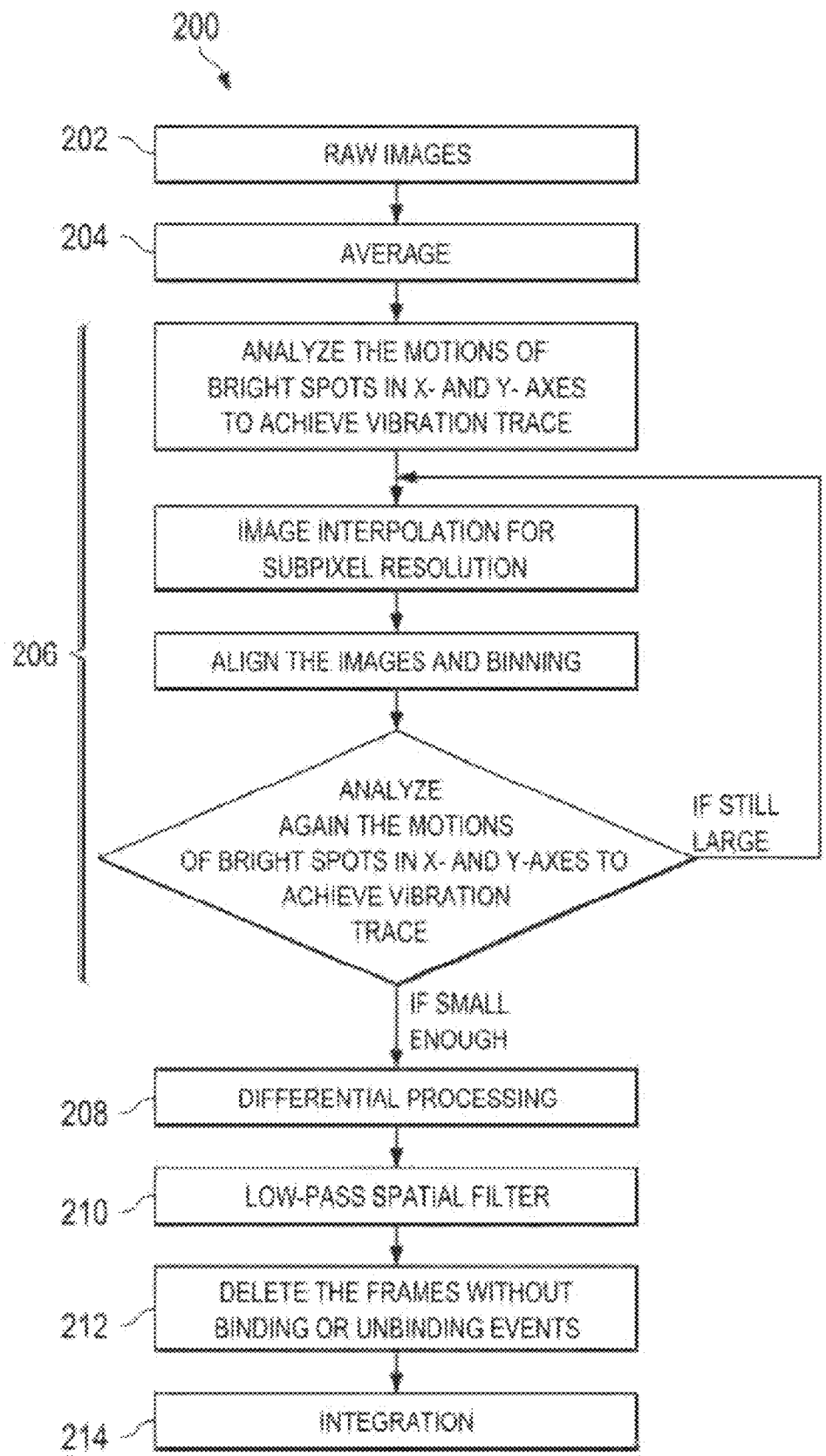
FIG. 2 is a schematic diagram showing exemplary steps performed by an image processing algorithm that are suitable for use with certain aspects disclosed herein.

Referring to FIG. 2, data processing protocol 200 of PSM images includes capturing 202 raw images, averaging 204 the image sequence captured at a high frame rate to remove pixel and other random noise in the images, introducing 206 a drift correction mechanism to correct the thermal and mechanical drift of the optical system, obtaining 208 differential images by subtracting the previous frame from the present frame, applying 210 a low-pass spatial filter to further minimize noise to the differential image sequence, removing 212 image frames without binding or unbinding events from the filtered differential image sequence, and integrating 214 the image sequence from first frame to $N^{th}$ frame to produce an image sequence, I(N).

The evanescent field associated with SPR decays exponentially from the surface (z-direction) into the solution. In other words, the scattering of the evanescent field by a finite size object depends on the distance (z) from the surface, and is given by, $$E_{EP} = E_0 \int_B^D \pi (Dr - z^2) e^{-1} dz,$$

where $E_O$ is a constant, z is distance from the gold surface, D is the diameter of the particle, and I is the decay length of the evanescent field, which is approximately 200 nm. Taking this z-distance dependence into account, the effective diameters of the 26, 44, 65, 99, 145, and 194 nm polystyrene nanoparticles used in aspects of this disclosure should be 25.4, 42.4, 61.6, 91.3, 129.1, and 166.3 nm, respectively. The need of this correction decreases with the size and the correction becomes insignificant for exosomes.

In addition to the exemplary systems disclosed herein, the present disclosure also provides various methods that can be implemented using those systems. In some embodiments, for example, the present disclosure provides methods of detecting an exosome (e.g., an unlabeled exosome). The methods include disposing a fluidic sample that comprises a plurality of exosomes in a chamber that is positioned at least partially within a fluidic device in which an inner surface of the chamber comprises at least a first set of exosome binding moieties that are capable of binding the exosomes. The methods also include binding at least a portion of the plurality of exosomes to at least a portion of the first set of exosome binding moieties to produce one or more surface-bound exosomes, introducing an incident light toward the inner surface of the chamber prior to, concurrent with, and/or after, producing the surface-bound exosomes, and detecting light scattered by the surface-bound exosomes to produce a set of exosome imaging data.

In other aspects, the present disclosure provides fluidic devices that are of use in performing the methods disclosed herein. In some embodiments, the fluidic devices include a body structure that defines at least one chamber disposed substantially within the body structure, wherein the chamber comprises a fluidic sample that comprises a plurality of exosomes and an inner surface that is coated with a metallic layer that is configured to create surface plasmon resonance when incident light is introduced toward the inner surface at a suitable incident angle via an outer surface of the chamber, and wherein the metallic layer comprises at least a first set of exosome binding moieties. In some embodiments, the fluidic device further comprises at least one inlet port and at least one outlet port that both fluidly communicate with the chamber. In some embodiments, the metallic layer comprises gold (Au). In some embodiments, the first set of exosome binding moieties is selected from the group consisting of: antibodies, aptamers, receptors, and/or the like.

In other aspects, the present disclosure also provides computer readable media that include non-transitory computer executable instruction which, when executed by at least electronic processor, perform at least: disposing a fluidic sample that comprises a plurality of exosomes in a chamber of a fluidic device, wherein the chamber comprises an inner surface that is coated with a metallic layer that is configured to create surface plasmon resonance when incident light is introduced toward the inner surface at a suitable incident angle via an outer surface of the chamber, and wherein the metallic layer comprises at least a first set of exosome binding moieties such that at least a portion of the plurality of exosomes bind to at least a portion of the first set of exosome binding moieties to produce one or more surface-bound exosomes; introducing an incident light from a light source toward the inner surface of the chamber; and detecting light scattered by the surface-bound exosomes over a duration to produce a set of exosome imaging data to thereby detect the exosomes biomolecules using a detector.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 208 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

EXAMPLE: LABEL-FREE IMAGING AND BIOMARKER ANALYSIS OF EXOSOMES AT MILLIMETRE SCALE WITH A PLASMONIC SCATTERING MICROSCOPY

Results and Discussion

Imaging Principle

Figure 3A:
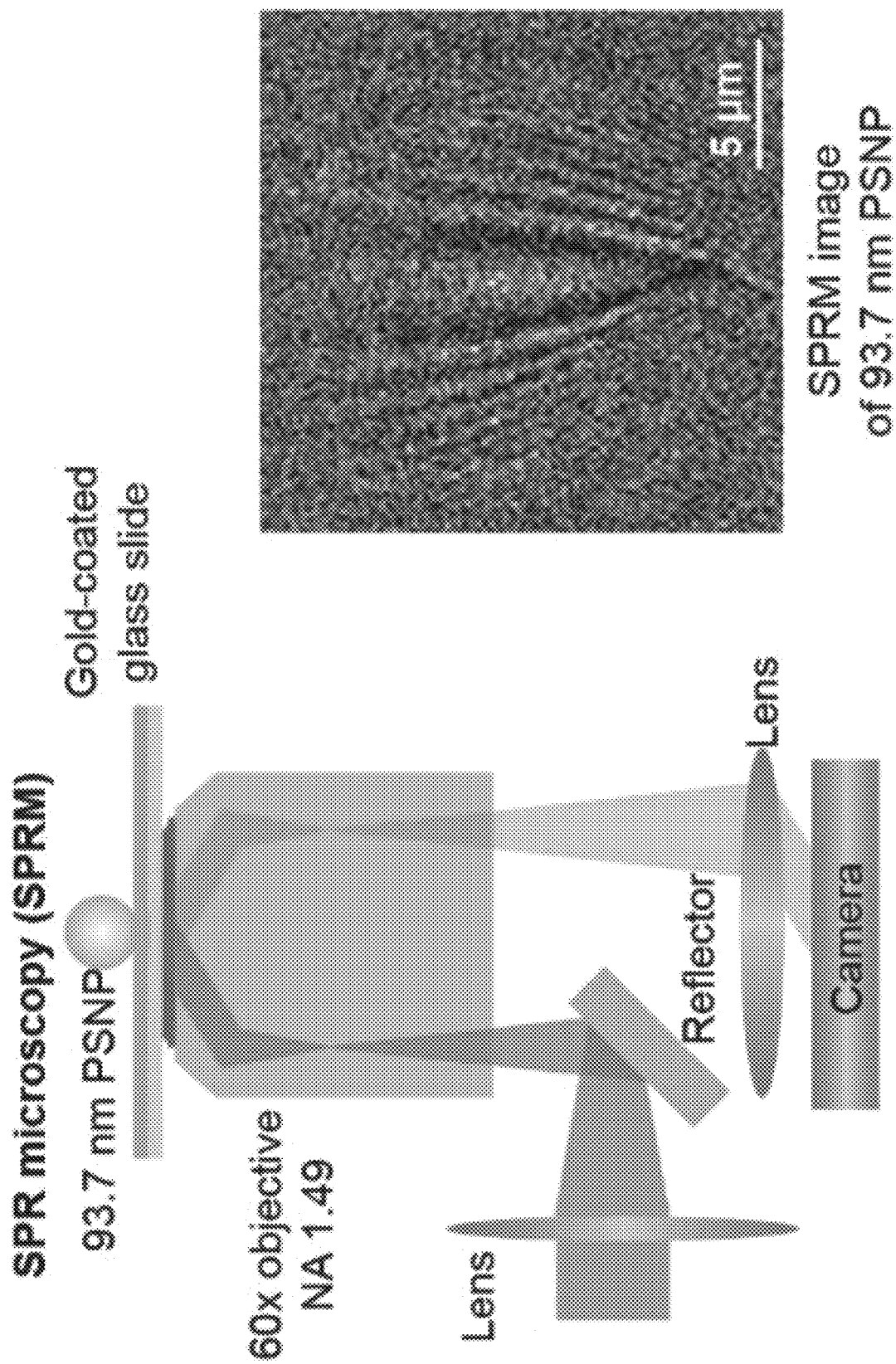
FIGS. 3A-3E. Simplified sketches of the optical setups for SPR microscopy (a) and PSM (b), and their images of one 93.7 nm polystyrene nanoparticle (PSNP). c, PSM images before and after the binding of 93.7 nm PSNP. d, PSM image intensity histograms of the PSNP with different diameters, where the solid lines are Gaussian fittings and the mean image intensities are marked. e, Mean PSM image intensity versus PSNP diameter. The z-distance dependence of surface plasmonic waves is considered. Incident light intensity is 0.1 W/cm$^2$ for SPR microscopy and 4 W/cm$^2$ for PSM.
Figure 3B:
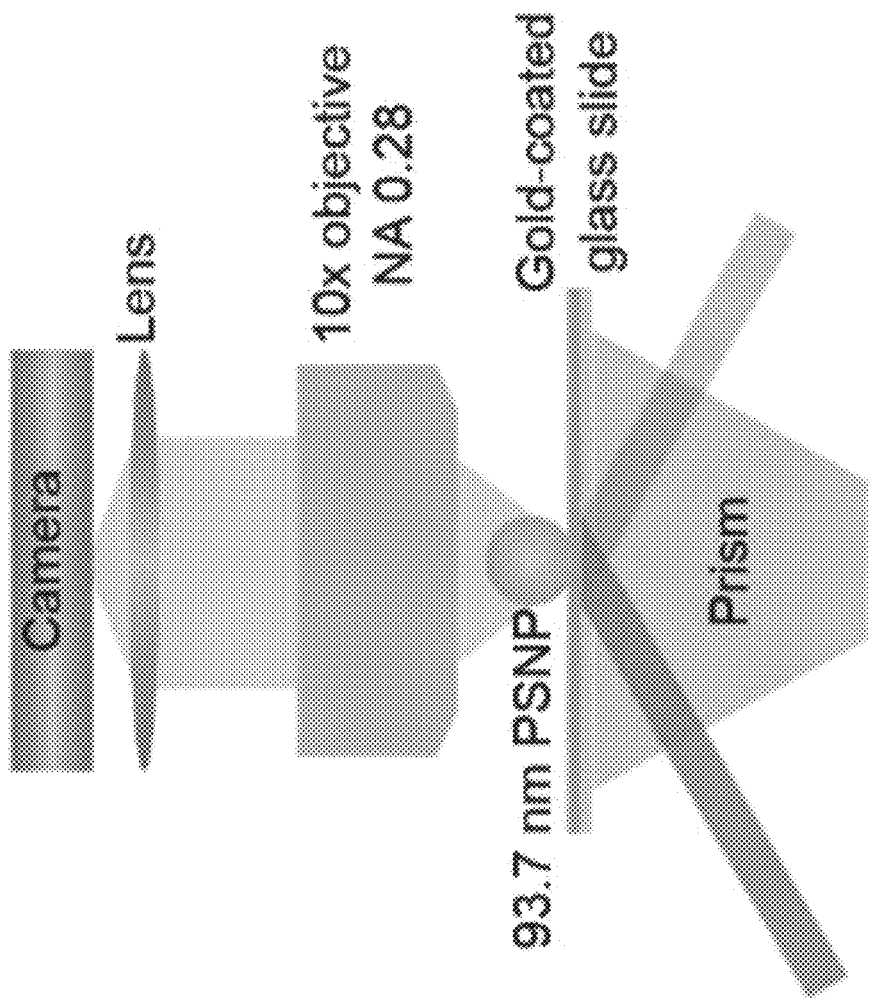

The SPR microscopy employs oblique illumination to excite the surface plasmonic wave on the gold-coated glass slide with a 60× oil-immersion objective (FIG. 3a), where the reflected light is recorded to form an SPR image. The image contrast is determined by the interference between the surface plasmonic wave and the plasmonic wave scattered by the analyte. The surface plasmonic wave has ~10 μm propagation length with the incident wavelength of 660 nm, leading to a parabolic tail following the spot at the location of the analyte in the SPR image, which is hard to be processed with regular software and can only be automatically analysed with specifically designed image processing algorithms. The PSM is constructed differently from the SPR microscopy by employing one objective to observe the plasmonic wave scattered by analytes on the top of the gold-coated glass slide (FIG. 3b). The PSM does not record the surface plasmonic waves. Thus, its point spread function is Gaussian distributed as classical optical microscopy, providing higher spatial resolution than SPR microscopy even with a low aperture numerical dry objective and making it easy to perform the image processing using conventional software such as ImageJ. In addition, the PSM can employ the prism configuration for a large illumination area and a low magnification objective, such as the 10× dry objective in this study, to achieve a large field of view. Considering that the incident light will occupy half view of the objective used in SPR microscopy, the PSM with a 10× dry objective will provide ~40 times larger field of view than SPR microscopy with the same imaging path. In this study, the PSM field of view is determined to be ~1.4 mm×1.0 mm by camera imaging area, which is over 100 times than the field of view of ~100 μm×100 μm in a classical NTA instrument, such as Malvern NS300. This indicates that the PSM can provide sufficient throughput for analysing the size distribution of highly heterogenous exosomes.

Figure 3C:
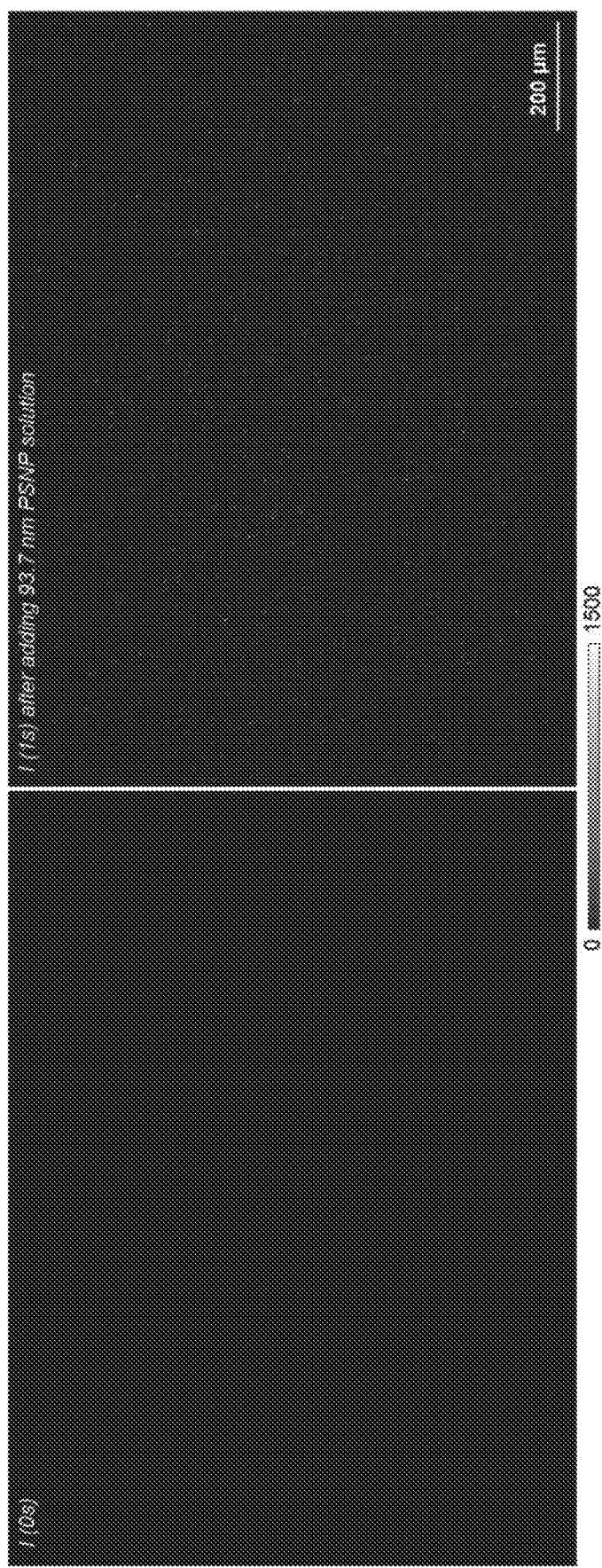
Figure 3D:
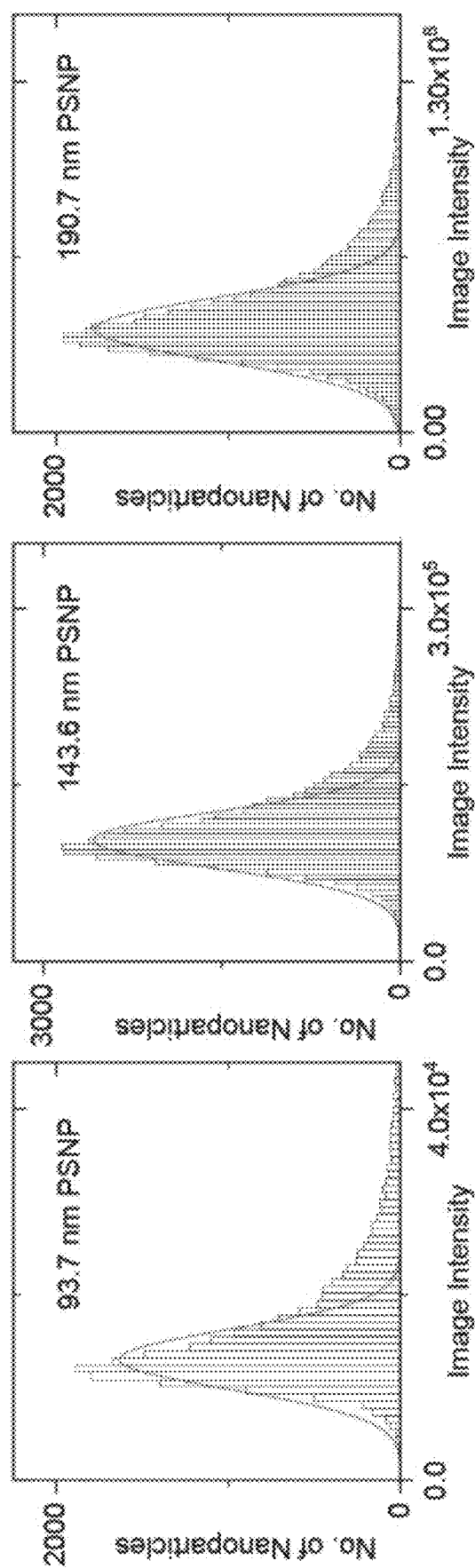
Figure 3E:
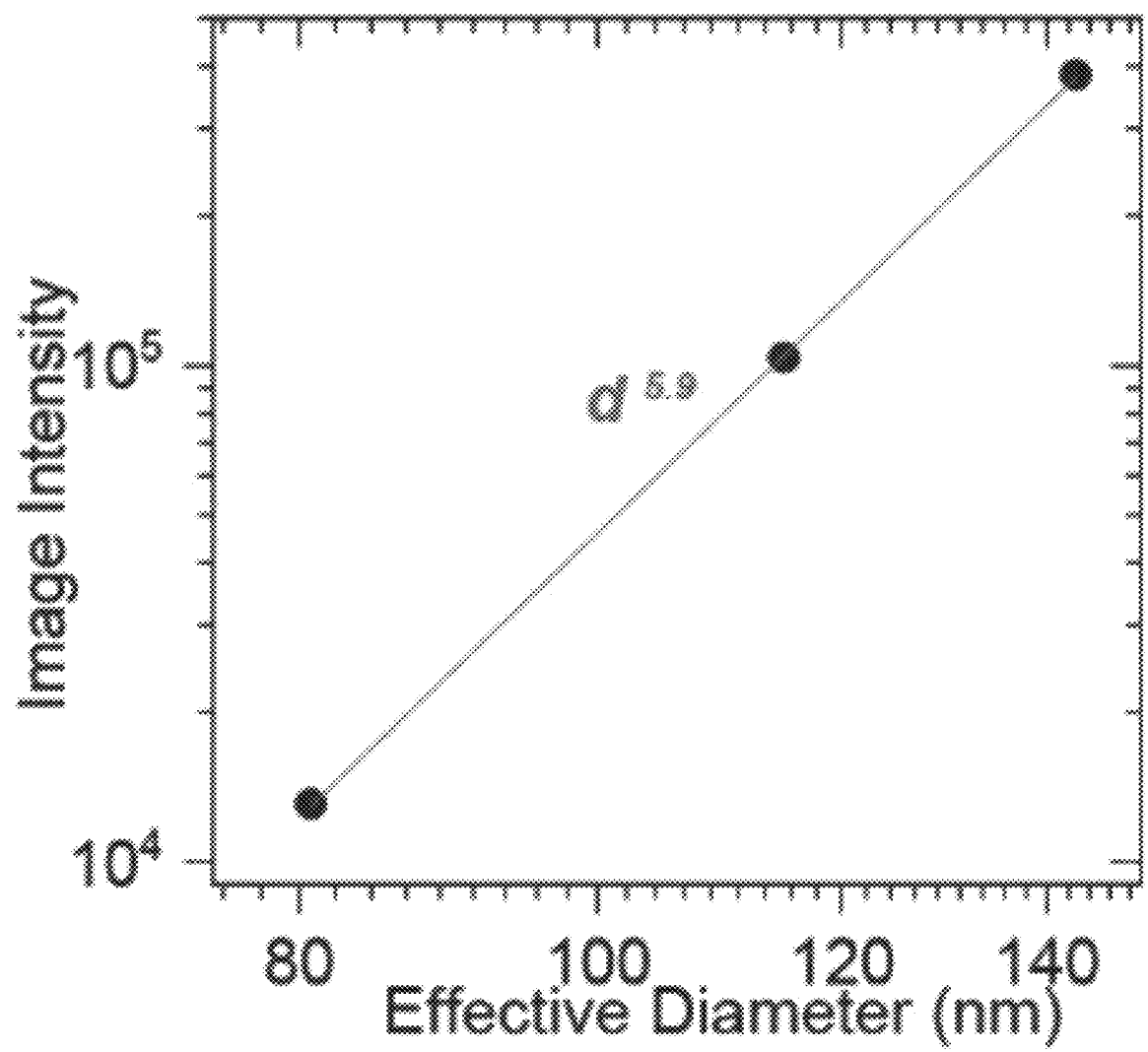

One key advantage of SPR technology is the high measurement sensitivity, which is usually defined by the signal-to-noise ratio (SNR) for imaging single nanoparticles and refractive index resolution for ensemble binding kinetics analysis. FIG. 3c presents the PSM images before and after the polystyrene nanoparticle binding after subtracting the background created by the gold surface roughness, showing that the PSM can provide sharp images over a millimetre scale field of view. To further estimate the imaging SNR, the PSM system was calibrated by imaging polystyrene nanoparticles with different diameters (FIG. 3d). The PSM image intensity was determined by integrating the intensities of all pixels covered by the bright spot created by the analyte. Taking the z-distance dependence of surface plasmonic wave into consideration, the PSM image intensity scales with d, where d is the diameter, and the exponent is close to six (FIG. 3e). This is expected because the light scattering dominates the PSM image contrast. Then, dividing the image intensity by the background fluctuation, the SNR of PSM measurement for imaging 93.7 nm polystyrene nanoparticles can be determined to be ~145, which is comparable to the state-of-art SPR microscopy. To estimate the refractive index resolution for ensemble measurements, the solutions with different refractive indices were measured serially, and the refractive index resolution of PSM can be estimated to be ~4.3×10$^{-6}$ RIU, which is also comparable to most ensemble SPR sensors.

Measurement of Exosome Binding to Anti-CD63

Figure 4A:
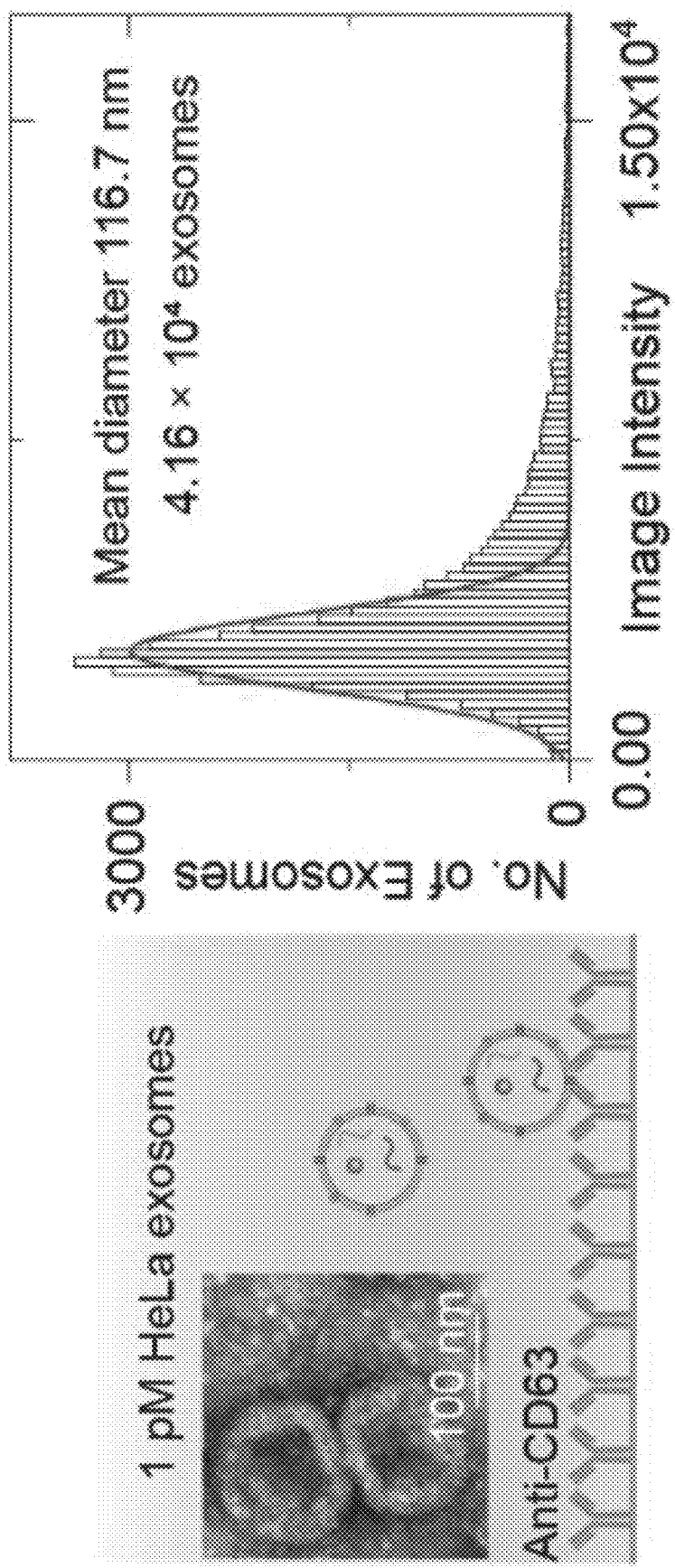
FIGS. 4A and 4B. a, TEM images of EVs from HeLa cells, schematic of exosome binding to anti-CD63 modified surface, and PSM image intensity histograms of the exosomes by individually counting the single binding events. The mean diameter of exosomes and sample size are also presented. b, Ensemble PSM measurement of 1 nM HeLa exosomes binding to the anti-CD63 antibody.

We firstly analysed the exosome size distribution by flowing the EV solution with the concentration of ~6.5×10$^{11}$ L$^{-1}$ (~1 pM) onto the anti-CD63 antibody modified PSM sensor surface and counting the single binding events. The EVs were extracted from the media culturing the HeLa cells by ultracentrifuge and resuspended in the PBS buffer (Methods). CD63 is a commonly used exosome surface protein marker, and thus anti-CD63 can recognize the exosomes from other kinds of EVs. Then the PSM intensities of exosome binding events were employed to construct the intensity histogram, and the mean intensity was achieved by Gaussian fitting (FIG. 4a). After considering the z-distance dependence of surface plasmonic wave and the refractive index difference between polystyrene nanoparticles and EV, the mean diameter of the exosomes can be estimated to be ~116.7 nm using the calibration curve shown in FIG. 3e. This value is in good agreement with the NTA analysis results and previously reported values, demonstrating the exosome size analysis capability of the PSM.

Then, the binding kinetics of exosome binding to anti-CD63 were analysed by firstly flowing the HeLa EV solution with the concentration of ~6.5×10$^{14}$ L$^{-1}$ (~1 nM) onto the anti-CD63 antibody modified PSM sensor surface, and then flowing PBS buffer over the sensor surface to allow study of unbinding of the exosomes from anti-CD63. The PSM image intensity variation relative to the background was recorded in real time to produce a binding kinetics curve. Fitting of the curves with the first-order binding kinetics model determines the association ($k_{on}$) and dissociation ($k_{off}$) rate constants, which are 2.9×10$^7$ M$^{-1}$ s$^{-1}$ and 4.5×10$^{-4}$ s$^{-1}$, respectively. From $k_{on}$ and $k_{off}$, the equilibrium dissociation constant ($K_D=k_{off}/k_{on}$) is determined to be 15.5 pM. The binding kinetics analysis shows that the exosomes can bind to anti-CD63 tightly, which is likely due to the multivalency bindings from multiple CD63 binding sites per exosome.

Measurement of WGA Binding to Exosomes

Figure 4B:
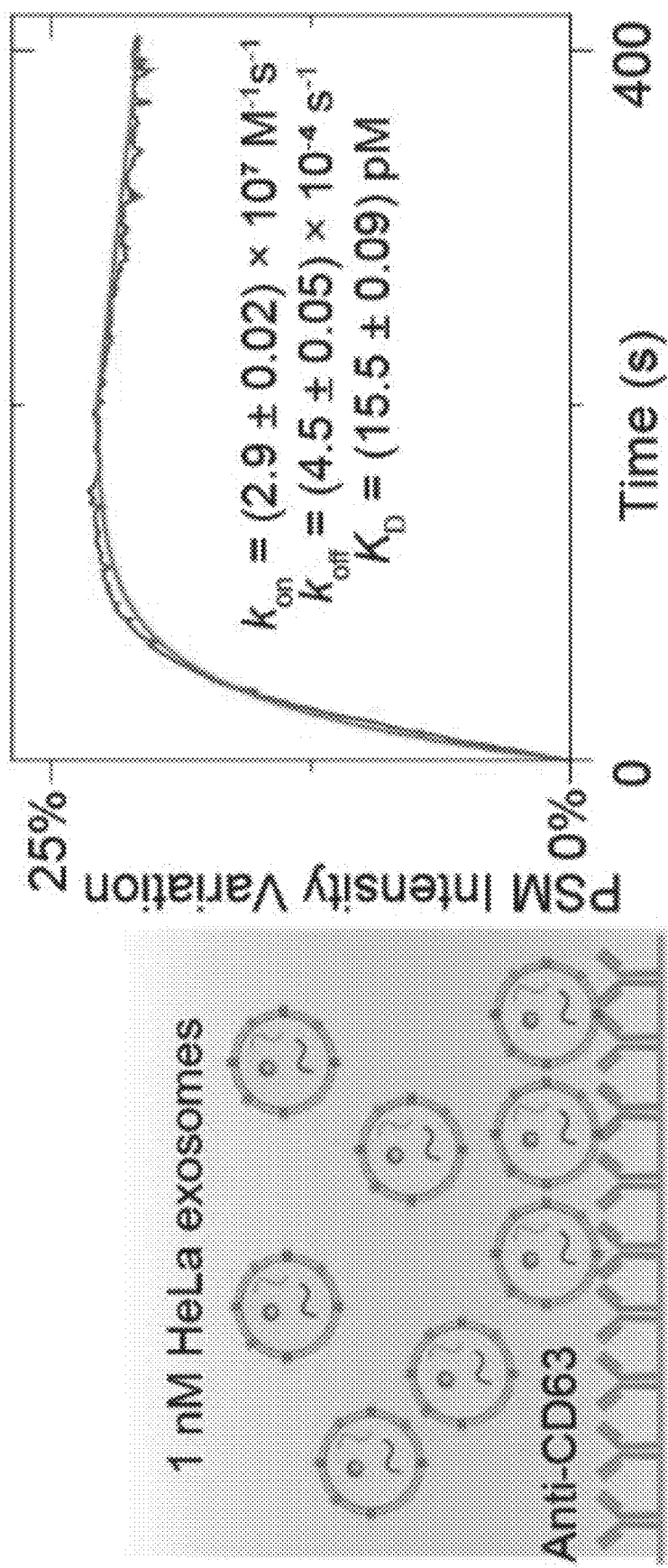
Figure 5A:
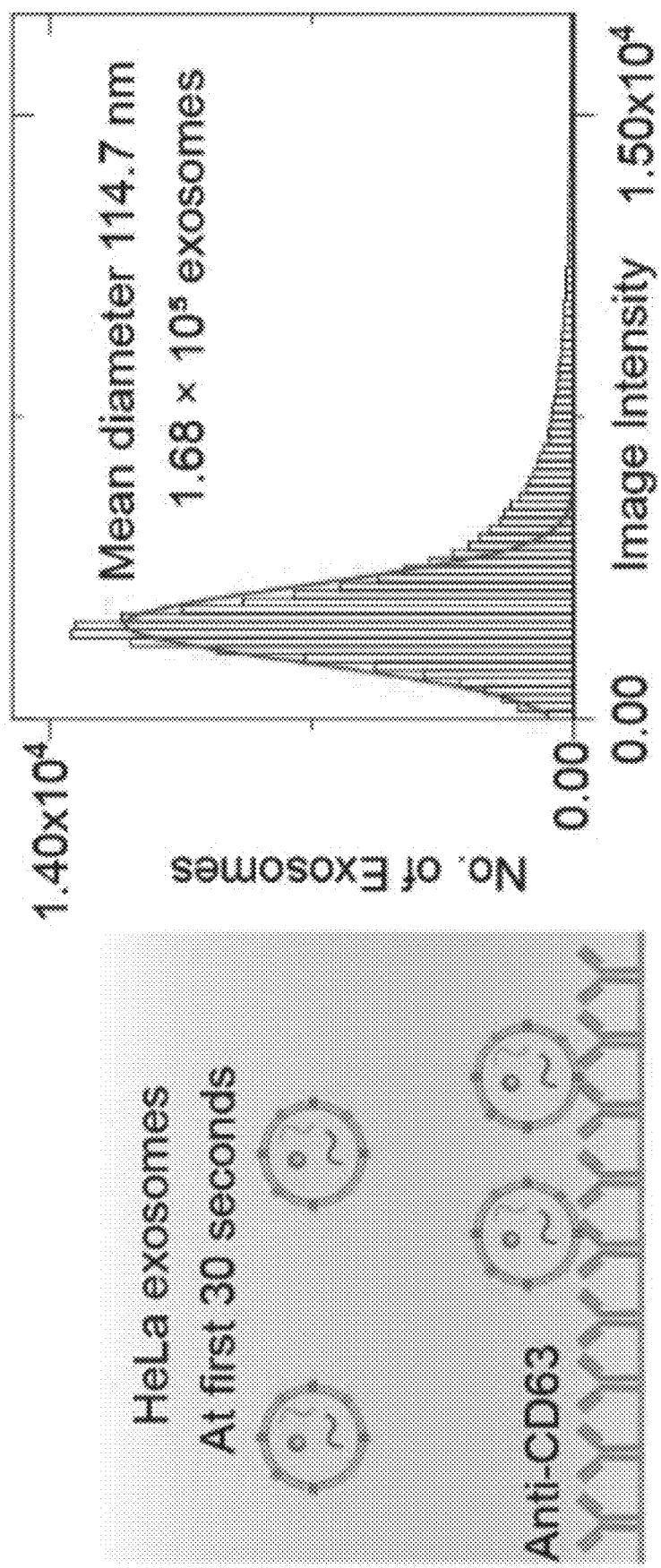
FIGS. 5A and 5B. a, PSM image intensity histograms of the exosomes by individually counting the single binding events at the first 30 seconds after flowing 1 nM HeLa EV solution onto the sensor surface. The exosomes are recognized by the anti-CD63 antibody immobilized on the gold surface. The mean diameter of exosomes and sample size are presented in the figure. b, Ensemble PSM measurement of WGA binding onto the N-acetylglucosamine and sialic acid groups on the surfaces of HeLa exosomes.
Figure 5B:
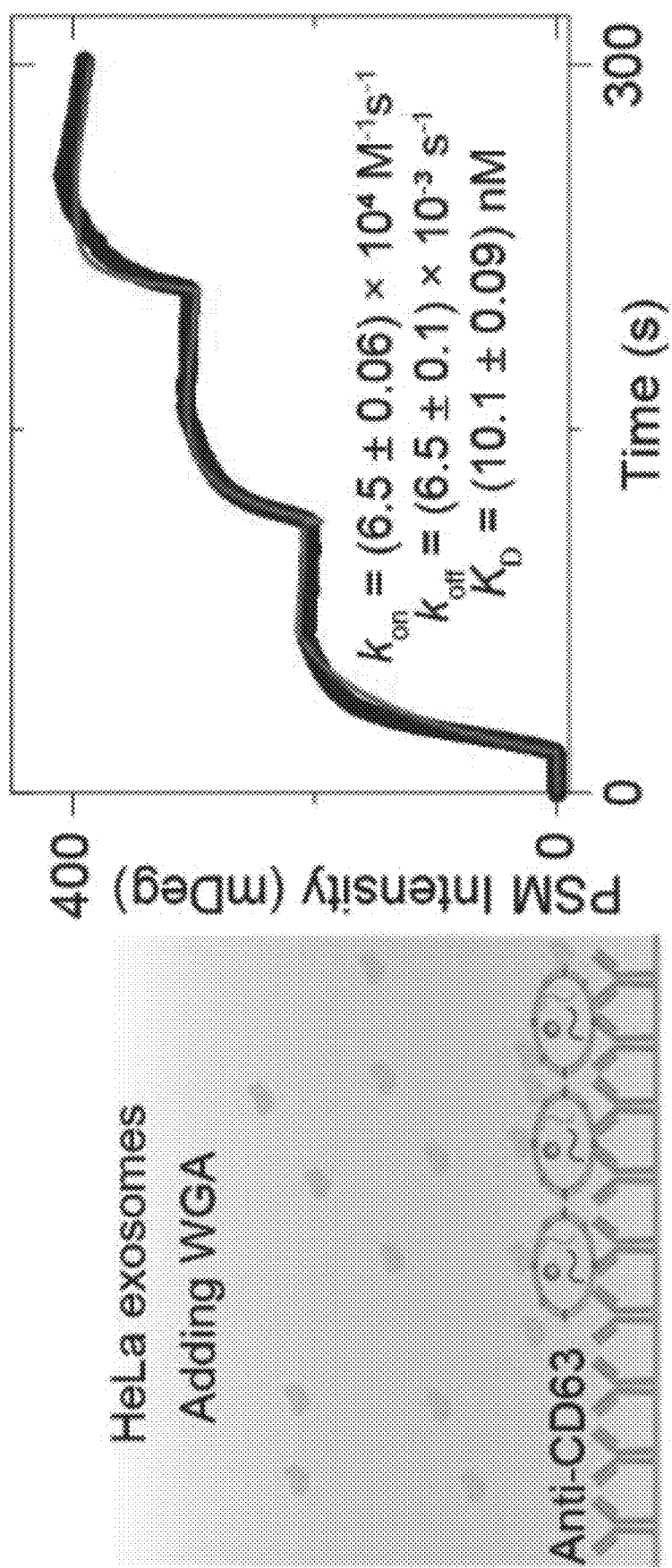

FIG. 4 has shown that the exosomes can bind to the surface tightly, which indicates that the sensor surface absorbing the exosomes can also provide stable background intensity, thus allowing study of the molecular interactions of the membrane proteins on the exosome surface. To demonstrate this, we first flowed the HeLa EV solution onto the anti-CD63 modified sensor surface and counted single binding events at the first 30 seconds to achieve the image intensity histogram (FIG. 5a). After Gaussian fitting, the exosomes have a mean diameter of ~114.7 nm, agreeing well with the NTA analysis results. Then, the PBS buffer was flowed onto the sensor surface for 20 minutes to remove the weakly binding vesicles and allow the vesicle deformations. Next, the incident angle was adjusted to the position allowing the maximum PSM intensity response to refractive index variations, and the 25 μg/mL wheat germ agglutinin (WGA) in PBS buffer was flowed onto the exosomes immobilized on the sensor surface to observe the WGA binding to N-acetylglucosamine and sialic acid groups of glycoproteins on the exosome surfaces. Last, the PBS buffer was flowed onto the exosomes to allow the dissociation of WGA from surface targets. WGA solutions of higher concentrations were measured subsequently: 50 μg/mL WGA solution, PBS buffer, 100 μg/mL WGA solution, and PBS buffer were flowed onto the exosomes in a serial. The PSM image intensity variations were calibrated to milli degree by the ensemble intensity difference between 100% and 80% PBS buffer, and the exosome response to the WGA association and dissociation was recorded in real time to produce a binding kinetics curve. Fitting of the curves with the kinetic titration mode determines the $k_{on}$ and $k_{off}$, which are 6.5×10$^4$ M$^{-1}$ s$^{-1}$ and 6.5×10$^{-3}$ s$^{-1}$, respectively. From $k_{on}$ and $k_{off}$, the $K_D$ is determined to be 10.1 nM. These values are in good agreement with the previously reported results measuring the WGA binding to membrane proteins, indicating that the PSM can measure the binding of proteins to the markers on the surface of exosomes immobilized on the sensor surface.

Biomarker Profiling

Figure 6A:
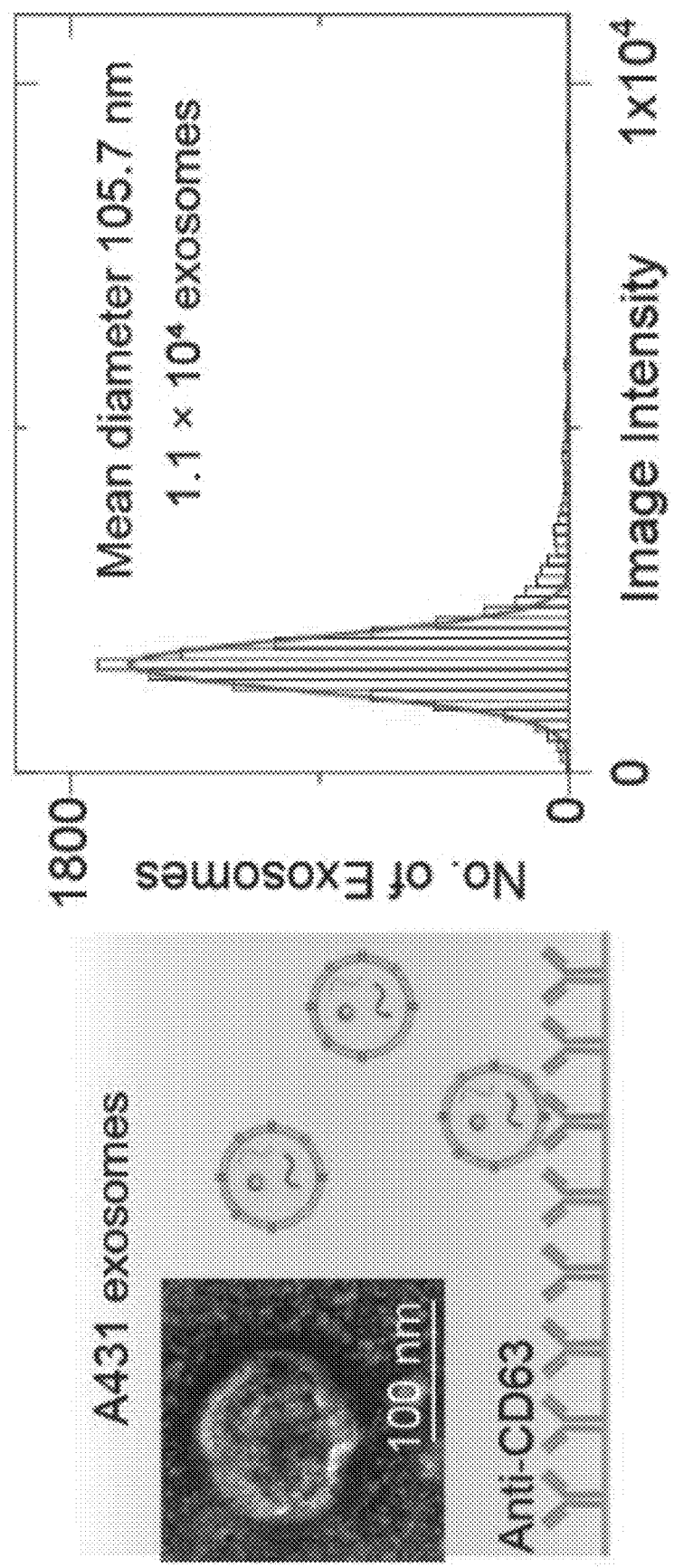
FIGS. 6A-6D. a, b TEM images of EV from A431 (a), and 293T(b) cells and PSM image intensity histograms of the exosomes by individually counting the single binding events. The exosomes are recognized by the anti-CD63 antibody immobilized on the gold surface. The mean diameter of exosomes and sample size are presented in the figure. c, d Ensemble PSM measurements of WGA, anti-CD81, and anti-EGFR binding to the target proteins on the surfaces of A431 (c), and 293T(d) exosomes. The protein levels are estimated by normalizing the target-associated changes to those of WGA targets.
Figure 6B:
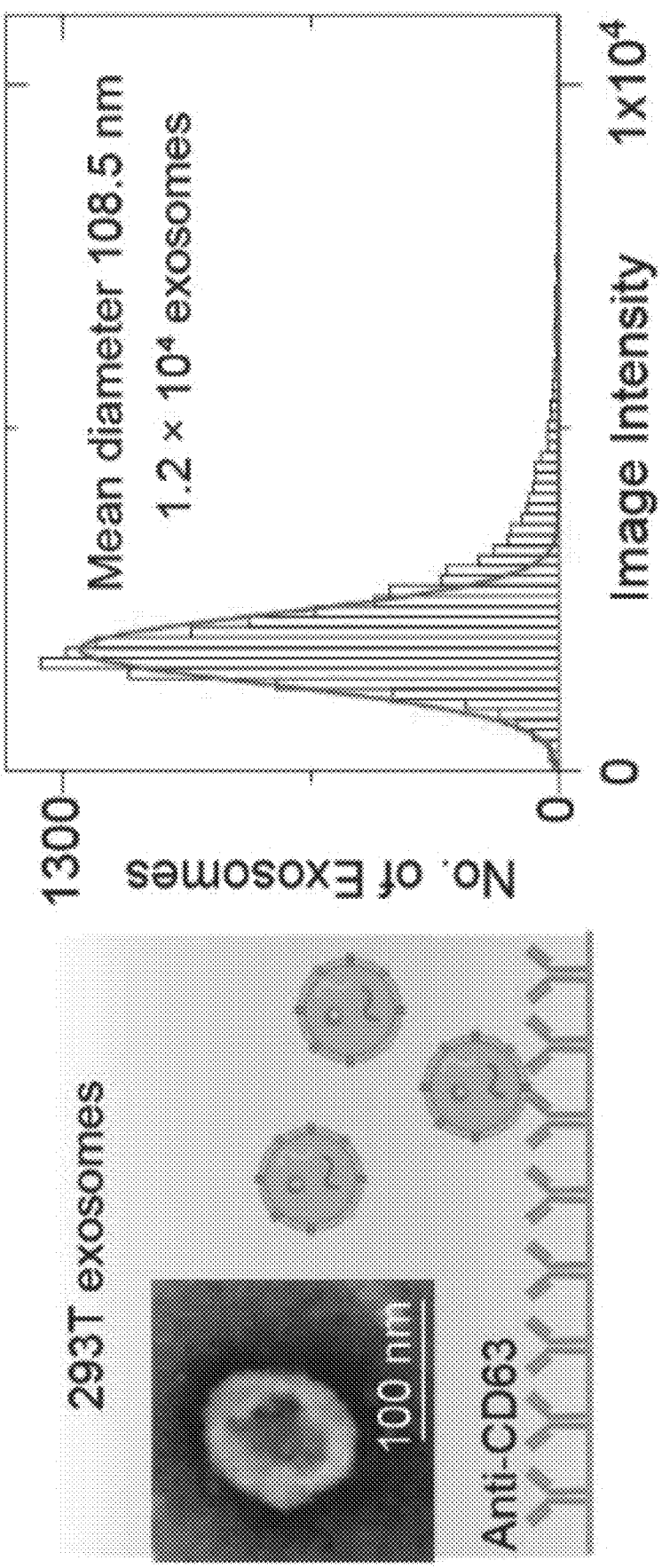
Figure 6C:
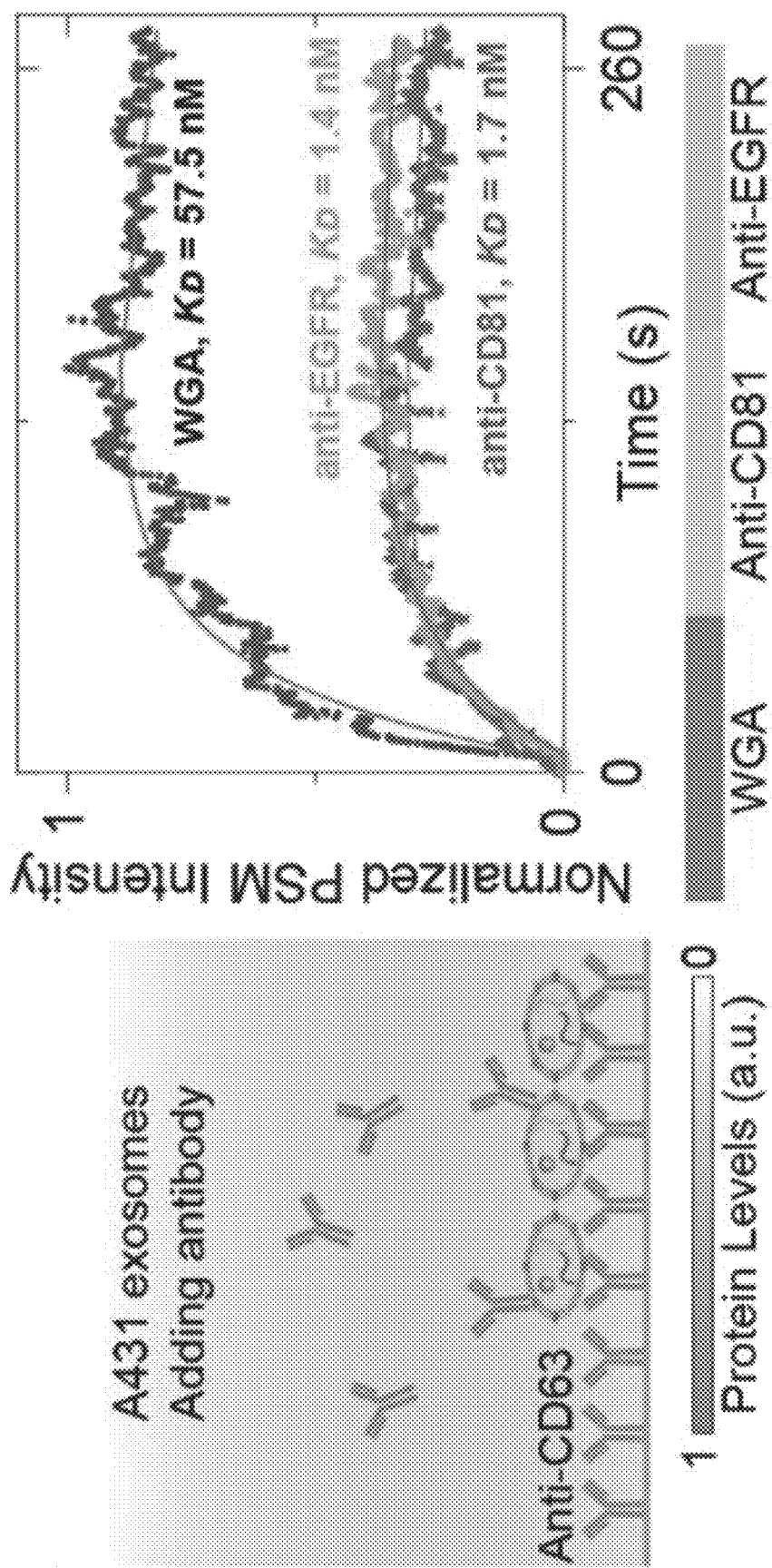
Figure 6D:
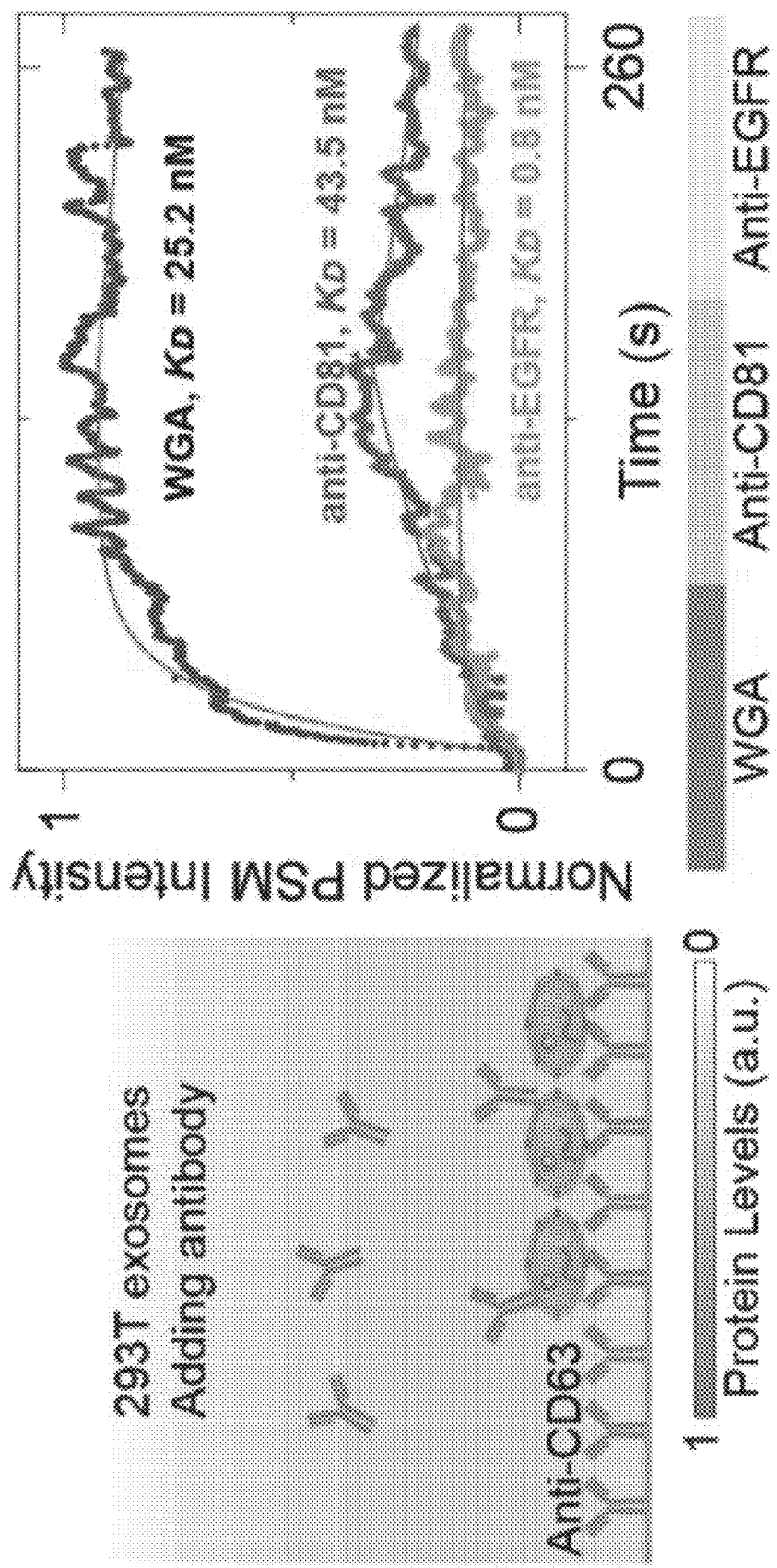

The content levels of exosome biomarkers can be estimated by normalizing the target associated changes to those of specific biomarkers abundant in and characteristic of exosomes, thus allowing us to quantify the biomarker profiles by monitoring the exosome response to different antibodies. To demonstrate this, we flowed the A431 and 293T EV solution onto the anti-CD63 modified sensor surface, and counted single binding events to achieve the image intensity histograms (FIGS. 6a and 6b). After Gaussian fitting, the exosomes have mean diameters of ~105.7 nm for A431 and ~108.5 nm for 293T, agreeing well with the NTA analysis results. Then 10 μg/mL anti-CD81 antibody, 10 μg/mL anti-epidermal growth factor receptor (anti-EGFR) antibody, and 100 μg/mL WGA solutions were flowed in a serial onto the A431 and 293T exosomes, respectively. Buffers were flowed in after each protein solution to measure the dissociation. The PSM image intensity response was recorded in real time to produce the binding kinetics curves (FIGS. 6c and 6d). The $k_{on}$, $k_{off}$ and $K_D$ values can be determined by fitting the curves with the first-order binding kinetics model as shown in Table 1. After normalizing the CD81 and EGFR associated changes to those of N-acetylglucosamine and sialic acid groups on the exosome surfaces, we can find that the CD81 content level is similar for both A431 and 293T exosomes, while the EGFR content level is much higher on A431 exosome surfaces than 293T exosome surfaces. This is expected because the CD81 is a membrane protein abundant in all exosomes, and the EGFR was overexpressed on A431 membranes, demonstrating that the PSM can measure content levels and binding kinetics of multiple biomarkers on exosome surfaces for biomarker profiling.

TABLE 1

Association rate constants ($k_{on}$), dissociation rate constants ($k_{off}$), and equilibrium constants ($K_D$) for different proteins binding to targets in the A431 and 293T exosomes.

| | $k_{on}$ (M$^{-1}$ s$^{-1}$) | $k_{off}$ (s$^{-1}$) | $K_D$ (nM) |
|---|---|---|---|
| Anti-CD81 to CD81 on A431 exosomes | 5.6 × 10$^5$ | 9.7 × 10$^{-4}$ | 1.7 |
| Anti-CD81 to CD81 on 293T exosomes | 6.9 × 10$^4$ | 3.0 × 10$^{-3}$ | 43.5 |
| Anti-EGFR to EGFR on A431 exosomes | 4.7 × 10$^5$ | 6.5 × 10$^{-4}$ | 1.4 |
| Anti-EGFR to EGFR on 293T exosomes | 1.2 × 10$^6$ | 9.0 × 10$^{-4}$ | 0.8 |
| WGA to N-acetylglucosamine and sialic acid groups on A431 exosomes | 1.2 × 10$^4$ | 6.9 × 10$^{-4}$ | 57.5 |
| WGA to N-acetylglucosamine and sialic acid groups on 293T exosomes | 2.1 × 10$^4$ | 5.3 × 10$^{-4}$ | 25.2 |

CONCLUSIONS

We have demonstrated that the PSM can provide a millimetre-scale field of view and high measurement sensitivity for label-free imaging and biomarker analysis of exosomes. The field of view is up to ~40 and ~100 times larger than the SPR microscopy and NTA instruments respectively, allowing sufficient throughput for exosome size analysis. In addition, the PSM eliminates the irregular particle scattering patterns, which are usually shown in SPR microscopy images, thus allowing the simple automatic processing with open-source ImageJ software. Furthermore, the binding kinetics and content levels of biomarkers of exosomes can be determined by monitoring the PSM image intensity variations during serially flowing the different antibodies onto the exosomes, providing a label-free and rapid solution for clinical multiplexed biomarker analysis and exploring the exosome surface protein binding properties. Finally, the PSM in this study can be easily constructed by adding commercially available components to the classical prism-based SPR systems, which have been widely used in commercial SPR products and home-built setups. Thus, this work provides an economical and powerful tool for clinical exosome analysis and exploration of fundamental issues such as exosome membrane protein properties.

Methods

Materials

Polystyrene nanoparticles were purchased from Bangs Laboratories (Fishers, Indiana, US). The No. 1 cover glasses (22×22 mm, Catalog No. 48366-067) and 150 mm culture dishes (Catalog No. 734-2322) were purchased from VWR (Radnor, PA, US). The gold pellets evaporation materials (Catalog No. EVMAU50SHOT) were purchased from Kurt J Lesker (Jefferson Hills, PA, US). Gold-coated glass slides were fabricated by coating a cover glass with 1 nm of Cr followed by 47 nm of gold via thermal evaporation (PVD75 E-beam/Thermal Evaporator, Kurt J. Lesker Company). Before coating, the gold surface was rinsed by ethanol and deionized water twice. The microfluidic ball valves were purchased from Cole-Parmer (Vernon Hills, IL, US). Stainless Steel Dispensing Needles (Catalog No. KDS2112P) were purchased from Weller (Besigheim, Germany). Dithiol Alkane Aromatic PEG6-COOH (Catalog No. SP35140) was purchased from Nanoscience Instruments (Phoenix, AZ, US). 20 mL syringe (Catalog No. 302830) was purchased from BD (Franklin Lakes, NJ, US). Microbore Tubes (Catalog No. AAD04103) were purchase from Tygon Tubing (Courbevoie, France). Ultracentrifuge bottles (Catalog No. 355622) were purchased from Beckman Coulter (Pasadena, CA, US). Dulbecco's Modified Eagle's Medium (DMEM, Cat. No. 20-2002) was purchased from ATCC (Manassas, VA, US). Fetal bovine serum (FBS, Cat. No. 10437036), and Trypsin-EDTA (0.05%, Cat. No. 25300120), 1-ethyl-3-(3-dimethylaminopropyl)carbodiimide hydrochloride (EDC, Catalog No. 22980) and Sulfo-NHS (N-hydroxysulfosuccinimide, Catalog No. 24510) were purchased from Thermo Scientific (Waltham, MA, US). The FBS was inactivated by heating to 56° C. for 30 minutes. Phosphate-Buffered Saline (PBS, Catalog No. 21-040-CV) and 25-cm2 flask (Cat. No. 3289) were purchased from Corning (Corning, NY, US). Penicillin-streptomycin mixture (Cat. No. DE17-602F) was purchased from Lonza (Basel, Switzerland). Wheat germ agglutinin (WGA, Cat. No. L0636) was purchase from Sigma-Aldrich (St. Louis, MO, US). Anti-EGFR (Cat. No. 05-101) monoclonal antibody and 0.1% gelatin solution (Cat. No. ES-006-B) were purchased from the EMD Millipore (Burlington, MA, US). Anti-CD63 (Cat. No. 556019) and anti-CD81 (Cat. No. 551112) monoclonal antibodies were purchased from the BD Biosciences (Franklin Lakes, NJ, US). The storage buffer for the proteins were removed with Zeba spin desalting columns (Cat. No. 89882, ThermoFisher) before experiments. Deionized water with resistivity of 18.2 MΩ cm-1 was filtered with 0.22-μm filters (Millex-GS, Catalog No. SLGSM33SS) from Sigma-Aldrich (St. Louis, MO, US) and used in all experiments.

Cell Culture and EV Isolation

The A431, HeLa, and 293T cells were purchased from ATCC. All the cells were grown in the culture media prepared by mixing DMEM with 10% FBS and 1% penicillin-streptomycin mixture. The culture media has been depleted of exosomes by ultracentrifugation at 120,000 g for 6 hours. We collected EVs released by HeLa cells with following steps. First, the HeLa cells were firstly cultured in a 25-cm$^2$ flask at 37° C. with 5% $CO_2$ and 70% relative humidity. Second, the HeLa cells were passaged with 0.05% Trypsin-EDTA when they were approximately 80% confluent in the flask and seeded into the 150 mm culture dishes. Third, the HeLa cells were passaged with 0.05% Trypsin-EDTA when they were approximately 80% confluent in the culture dishes and seeded into another ten of 150 mm culture dishes. Fourth, after culturing for 3 days, the supernatant was collected from the ten of 150 mm culture dishes. Fifth, dead cells were depleted from the supernatant by centrifugation at 125 g for 5 minutes. Sixth, cell debris were depleted from the supernatant by centrifugation at 4000 g for 30 minutes. Seventh, microvesicles were depleted from the supernatant by centrifugation at 10000 g for 30 minutes. Eighth, EVs were collected by ultracentrifugation at 120,000 g for 4 hours 15 minutes. Ninth, EVs were resuspended by washing the ultracentrifugation bottle wall by ten times and immersion over night with PBS. Tenth, EVs were collected from the solution by ultracentrifugation at 120,000 g for 4 hours 15 minutes, and resuspended by washing the ultracentrifugation bottle wall by ten times and immersion over night with 1 mL PBS. Eleventh, aliquot the EV solution and store them at −80° C. The EVs released by A431 and 293T cells were collected with the same steps.

TEM

For negative-stain TEM analysis, 5 μl of EV solution was placed on a formvar/carbon-coated grid and allowed to settle for 1 min. Then, the sample was negative stained with four successive drops of 1.5% uranyl acetate and washed with distilled water. After air drying, grids were imaged with a Philips CM 12 transmission electron microscope (TEM).

NTA

EV concentration and size distribution were determined using a NanoSight NS300 (Malvern Panalytical, Malvern, UK) equipped with a green laser and a high sensitivity sCMOS camera following the manuals. Each sample was diluted 10 to 1000-fold in PBS buffer to achieve ~50 particles in one frame for optimal counting and then introduced to the instrument using a micropump with a 1 mL syringe.

Experimental Setup

The PSM was constructed on a classical prism coupled SPR system. Light from a laser diode with center wavelength of 660 nm (OBIS LX 660 nm 75 mW Laser System, Fiber Pigtail, Coherent, Santa Clara, CA, US) was conditioned by three lenses configured in a 4-f arrangement, and then excite the SPR on the gold coated glass slide placed on a prism (Cat. No. 49431, Edmund optics, Barrington, NJ, US). The scattered surface plasmonic waves were collected by a 10× dry objective (NA 0.28, MOTIC, Xiamen, China), and imaged by a USB 3.0 CMOS camera (MC124MG-SY, XIMEA, Münster, Germany). A flow cell is designed for sample delivery. A rectangle double sided tape (9628B, 3M, Saint Paul, MN, US) spacer is bound between a No. 1 cover glass with two 1 mm drilled holes (as inlet and outlet) and a gold-coated glass slide to form a flow cell. The cell height is set to be ~50 μm by controlling the thickness of double-sided tape. Two PDMS blocks with holes created by disposable biopsy punch 0.75 mm with Plunger (Catalog No. 18271 P, Robbins Instruments, Houston, TX, US) were attached to the cover glass after plasma cleaning and incubated at 90° C. for 1 hour to fix the tubes. A push-pull two-way flow mode was configured for sample delivery. The sample was placed in a tube higher than the flow cell, thus allowing the gravity to push the samples thorough the sensor surface. At the same time, a syringe pump (TSD01-01, Lead Fluid, Baoding, China) connected to the outlet was employed to pull the samples to eliminate the flow rate gradient, thus decreasing the pressure on the flow cell wall. This configuration does not require strong seal, thus allowing easy construction of the flow cell.

Surface Functionalization

Gold-coated glass slides were incubated in 1 mM dithiol Alkane Aromatic PEG6-COOH in PBS buffer over night to be modified with carboxyl groups. Then the surface was incubated in 0.05 M NHS/0.2 M EDC for 30 min to activate the carboxyl groups. After rinsing with PBS, 33 nM anti-CD63 was applied to the surface and incubated for 1 hour to allow immobilization. At last, the surface was incubated in 1 mg/ml BSA for 10 min to block non-specific binding sites.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A method of detecting an exosome, the method comprising:

disposing a fluidic sample that comprises a plurality of exosomes in a chamber that is positioned at least partially within a fluidic device, wherein at least one inner surface of the chamber comprises at least a first set of exosome binding moieties that are capable of binding the exosomes;

binding at least a portion of the plurality of exosomes to at least a portion of the first set of exosome binding moieties to produce one or more surface-bound exosomes;

introducing an incident light toward the inner surface of the chamber prior to, concurrent with, and/or after, producing the surface-bound exosomes; and, detecting light scattered by the surface-bound exosomes to produce a set of exosome imaging data, thereby detecting the exosome.

2. The method of claim 1, wherein:

the plurality of exosomes is unlabeled; and/or, the plurality of exosomes comprises one or more biomarkers and wherein the method comprises quantifying the biomarkers and/or binding kinetics thereof using the set of exosome imaging data.

3. The method of claim 1, wherein the first set of exosome binding moieties are selected from the group consisting of: a first set of antibodies, a first set of aptamers, and a first set of receptors.

4. The method of claim 1, comprising:

detecting the light scattered by the surface-bound exosomes over a duration to produce the set of exosome imaging data;

detecting the light scattered by the surface-bound exosomes using at least one plasmonic scattering microscopy (PSM) technique;

producing the surface-bound exosomes and detecting the light scattered by the surface-bound exosomes substantially simultaneously; and/or, detecting the light scattered by the surface-bound exosomes in substantially real-time.

5. The method of claim 1, further comprising counting a number of individual surface-bound exosomes over the duration to produce a count and fitting the count with a binding model to determine kinetic constants and/or at least one affinity value.

6. The method of claim 1, comprising differentiating at least some of the plurality of exosomes from other extracellular vesicles in the fluidic sample using the set of exosome imaging data.

7. The method of claim 1, comprising determining a cellular origin of one or more of the surface-bound exosomes using the set of exosome imaging data.

8. The method of claim 1, comprising determining one or more properties of surface-bound exosomes selected from the group consisting of: an exosome size distribution, an exosome biomarker identity, and an exosome biomarker binding property.

9. The method of claim 1, wherein the set of exosome imaging data comprises image intensity variation.

10. The method of claim 1, further comprising disposing at least a second set of exosome binding moieties that are capable of binding the exosomes in the chamber prior to, concurrent with, or after producing the surface-bound exosomes, wherein at least a portion of the second set of exosome binding moieties bind to at least some of the plurality of exosomes.

11. The method of claim 1, comprising flowing different sets of exosome binding moieties in series at least partially through the chamber.

12. The method of claim 1, wherein the inner surface of the chamber is coated with a metallic layer.

13. The method of claim 1, wherein:
an incident angle of the incident light is selected to create surface plasmon resonance on the metallic layer; and/or,
a roughness of the inner surface is selected such that light scattered by the inner surface interferes with at least some of the light scattered by the surface-bound exosomes.

14. The method of claim 1, wherein the detecting step comprises detecting evanescent light scattered by individual surface-bound exosomes.

15. A fluidic device, comprising a body structure that defines at least one chamber disposed substantially within the body structure, wherein the chamber comprises a fluidic sample that comprises a plurality of exosomes and an inner surface that is coated with a metallic layer that is configured to create surface plasmon resonance when incident light is introduced toward the inner surface at a suitable incident angle via an outer surface of the chamber, and wherein the metallic layer comprises at least a first set of exosome binding moieties.

16. The fluidic device of claim 15, wherein the metallic layer comprises gold (Au).

17. The fluidic device of claim 15, wherein the first set of exosome binding moieties is selected from the group consisting of: antibodies, aptamers, and receptors.

18. A system for detecting exosomes, comprising:
a fluidic device receiving area configured to receive a fluidic device that comprises a body structure that defines at least one chamber disposed substantially within the body structure, wherein the chamber comprises an inner surface that is coated with a metallic layer that is configured to create surface plasmon resonance when incident light is introduced toward the inner surface at a suitable incident angle via an outer surface of the chamber, and wherein the metallic layer comprises at least a first set of exosome binding moieties;
a light source configured to introduce an incident light toward the fluidic device receiving area;
a detector configured to collect light scattered by surface-bound exosomes when the fluidic device is received in the fluidic device receiving area and the incident light is introduced from the light source; and
a controller that comprises, or is capable of accessing, computer readable media comprising non-transitory computer-executable instructions which, when executed by at least one electronic processor, perform at least:
disposing a fluidic sample that comprises a plurality of exosomes in the chamber of the fluidic device such that at least a portion of the plurality of exosomes bind to at least a portion of the first set of exosome binding moieties to produce one or more surface-bound exosomes when the fluidic device is received in the fluidic device receiving area;
introducing the incident light from the light source at the suitable incident angle toward the inner surface of the chamber when the fluidic device is received in the fluidic device receiving area; and,
detecting light scattered by the surface-bound exosomes over a duration to produce a set of exosome imaging data to thereby detect the exosomes using the detector when the fluidic device is received in the fluidic device receiving area.

19. The system of claim 18, wherein the set of exosome imaging data comprises video data.

20. The system of claim 18, wherein the non-transitory computer-executable instructions which, when executed by the electronic processor, further perform at least:
counting a number of individual surface-bound exosomes over the duration to produce a count and fitting the count with a binding model to determine kinetic constants and/or at least one affinity value;
quantifying biomarkers of the exosomes and/or binding kinetics thereof using the set of exosome imaging data;
differentiating at least some of the plurality of exosomes from other extracellular vesicles in the fluidic sample using the set of exosome imaging data;
determining a cellular origin of one or more of the surface-bound exosomes using the set of exosome imaging data;
determining one or more properties of surface-bound exosomes selected from the group consisting of: an exosome size distribution, an exosome biomarker identity, and an exosome biomarker binding property;
disposing at least a second set of exosome binding moieties that are capable of binding the exosomes in the chamber prior to, concurrent with, or after producing the surface-bound exosomes, wherein at least a portion of the second set of exosome binding moieties bind to at least some of the plurality of exosomes; and/or,
flowing different sets of exosome binding moieties in series at least partially through the chamber.

* * * * *